(12) United States Patent
Forsell

(10) Patent No.: US 9,486,318 B2
(45) Date of Patent: Nov. 8, 2016

(54) HIP JOINT DEVICE

(76) Inventor: Peter Forsell, Bouveret (CH)

(\*) Notice: Subject to any disclaimer, the term of this patent is extended or adjusted under 35 U.S.C. 154(b) by 147 days.

(21) Appl. No.: 13/382,708

(22) PCT Filed: Jul. 12, 2010

(86) PCT No.: PCT/SE2010/050804
§ 371 (c)(1),
(2), (4) Date: Jan. 6, 2012

(87) PCT Pub. No.: WO2011/005188
PCT Pub. Date: Jan. 13, 2011

(65) Prior Publication Data
US 2012/0116529 A1 May 10, 2012

Related U.S. Application Data

(60) Provisional application No. 61/229,738, filed on Jul. 30, 2009, provisional application No. 61/229,739, filed on Jul. 30, 2009, provisional application No. 61/229,743, filed on Jul. 30, 2009, provisional (Continued)

(30) Foreign Application Priority Data

| Jul. 10, 2009 | (SE) | ........................................ | 0900957 |
| Jul. 10, 2009 | (SE) | ........................................ | 0900958 |
| Jul. 10, 2009 | (SE) | ........................................ | 0900959 |
| Jul. 10, 2009 | (SE) | ........................................ | 0900960 |
| Jul. 10, 2009 | (SE) | ........................................ | 0900962 |
| Jul. 10, 2009 | (SE) | ........................................ | 0900963 |
| Jul. 10, 2009 | (SE) | ........................................ | 0900965 |
| Jul. 10, 2009 | (SE) | ........................................ | 0900966 |
| Jul. 10, 2009 | (SE) | ........................................ | 0900968 |
| Jul. 10, 2009 | (SE) | ........................................ | 0900969 |
| Jul. 10, 2009 | (SE) | ........................................ | 0900970 |
| Jul. 10, 2009 | (SE) | ........................................ | 0900972 |
| Jul. 10, 2009 | (SE) | ........................................ | 0900973 |
| Jul. 10, 2009 | (SE) | ........................................ | 0900974 |
| Jul. 10, 2009 | (SE) | ........................................ | 0900976 |
| Jul. 10, 2009 | (SE) | ........................................ | 0900978 |
| Jul. 10, 2009 | (SE) | ........................................ | 0900981 |

(51) Int. Cl.
*A61F 2/36* (2006.01)
*A61F 2/30* (2006.01)

(52) U.S. Cl.
CPC ............... *A61F 2/3603* (2013.01); *A61F 2/36* (2013.01); *A61F 2/3601* (2013.01);
(Continued)

(58) Field of Classification Search
CPC .......... A61B 17/7258; A61B 17/7266; A61B 17/7275
USPC ............ 623/23.12–23.14, 23.26; 606/63, 68, 606/313
See application file for complete search history.

(56) References Cited

U.S. PATENT DOCUMENTS 3,846,846 A * 11/1974 Fischer ...................... 623/23.18
4,520,511 A * 6/1985 Gianezio et al. .......... 623/22.46
(Continued)

FOREIGN PATENT DOCUMENTS

| CH | 426096 | 6/1966 |
| DE | 3701198 A1 | 7/1988 |

(Continued)

OTHER PUBLICATIONS

Abstract of EP0843298A2 retrieved from Espacenet on Jun. 6, 2016.*

(Continued)

*Primary Examiner* — Thomas J Sweet
*Assistant Examiner* — Megan Wolf

(57) ABSTRACT

A medical device for fixation in a femoral bone of a patient is provided, the medical device comprises: a connecting portion adapted to be connected to a prosthetic hip joint contacting portion, an expanding portion, and a bone contacting surface on the expanding portion. The expanding portion could be adapted to be at least partially inserted into the femoral bone of a patient and to expand within the femoral bone, such that the bone contacting surface is placed in contact with the inside of the femoral bone for fixating the medical device to the femoral bone. By the fixation using an expanding portion a sturdy fixation is achieved without the need to go into or penetrate bone, or the need for fixation using bone cement.

15 Claims, 21 Drawing Sheets

Related U.S. Application Data application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(52) U.S. Cl.
CPC ............. *A61F 2002/30205* (2013.01); *A61F 2002/30405* (2013.01); *A61F 2002/30462* (2013.01); *A61F 2002/30471* (2013.01); *A61F 2002/30507* (2013.01); *A61F 2002/30565* (2013.01); *A61F 2002/30579* (2013.01); *A61F 2002/30729* (2013.01); *A61F 2002/30841* (2013.01); *A61F 2002/365* (2013.01); *A61F 2002/3615* (2013.01); *A61F 2002/3631* (2013.01); *A61F 2002/3686* (2013.01)

(56) References Cited

U.S. PATENT DOCUMENTS

| 5,116,378 | A | 5/1992 | Carbone | |
|---|---|---|---|---|
| 6,355,069 | B1 | 3/2002 | DeCarlo | |
| 6,554,833 | B2 * | 4/2003 | Levy et al. | 606/63 |
| 8,211,185 | B2 * | 7/2012 | Linares | 623/23.44 |
| 2004/0193276 | A1 * | 9/2004 | Maroney et al. | 623/19.14 |

FOREIGN PATENT DOCUMENTS

| DE | 9402598U1 | U1 | 4/1994 |
|---|---|---|---|
| DE | 19731298A1 | A1 | 11/1999 |
| EP | 0843298A2 | A2 | 5/1998 |
| EP | 0982011 | | 3/2000 |
| FR | 2653660 | | 5/1991 |
| RU | 2083172C1 | C1 | 7/1997 |
| WO | WO 2008/154762 | | 12/2008 |
| WO | 2011082244 | A2 | 7/2011 |

OTHER PUBLICATIONS

Translation of RU2083172 retrieved from Espacenet on Jun. 6, 2016.*
Translation of DE19731298 retrieved from Espacenet on Jun. 6, 2016.*
Translation of DE3701198 retrieved from Espacenet on Jun. 6, 2016.*
Translation of DE9402598 retrieved from Espacenet on Jun. 6, 2016.*
International Search Report for PCT/SE2010/050804, mailed Oct. 25, 2010.

* cited by examiner

A - A

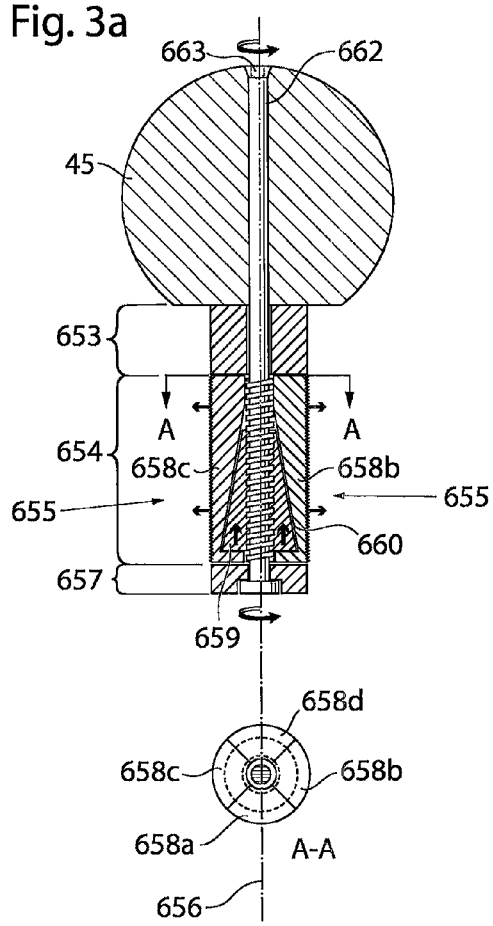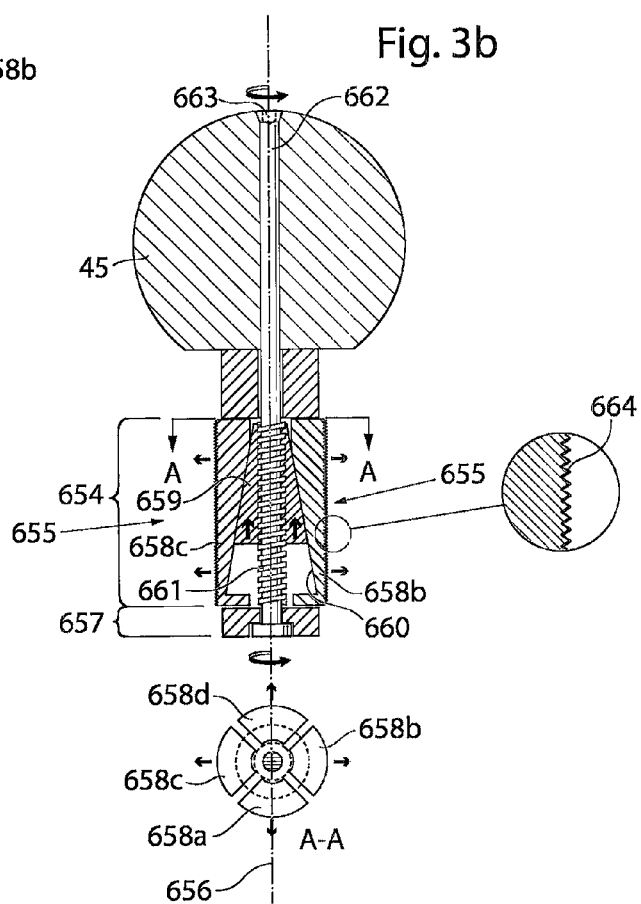

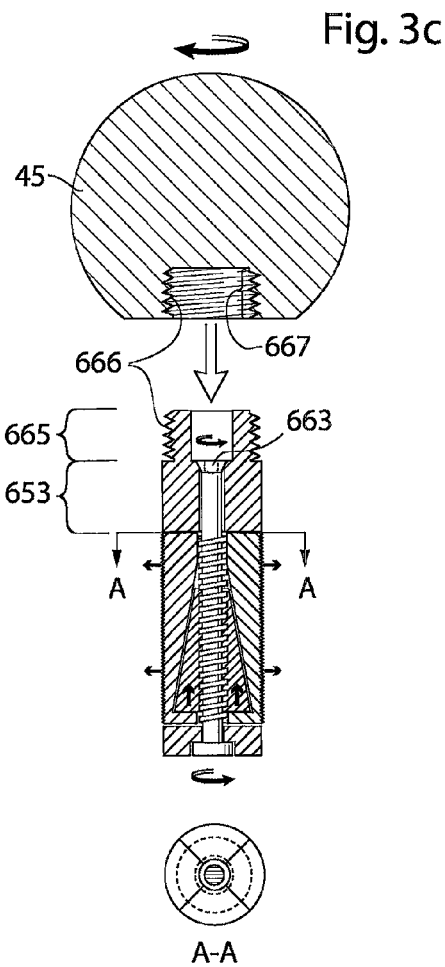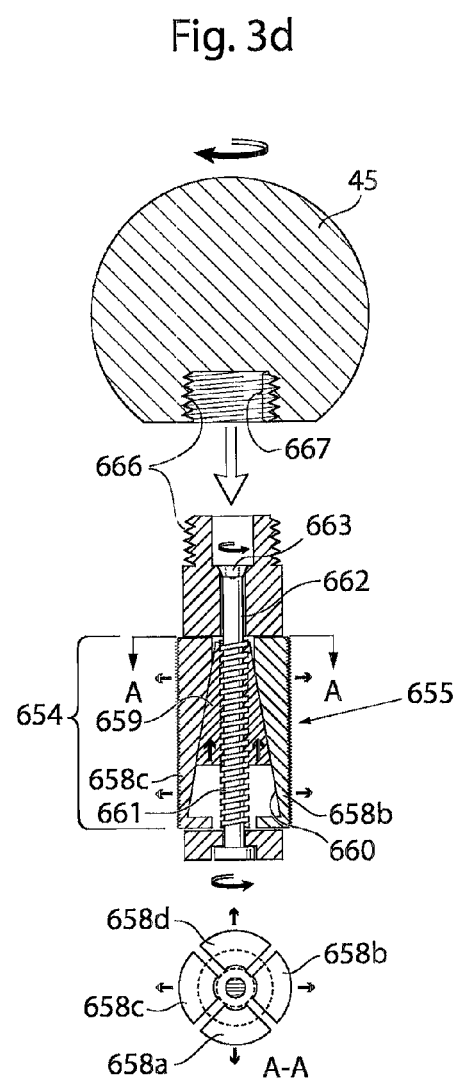

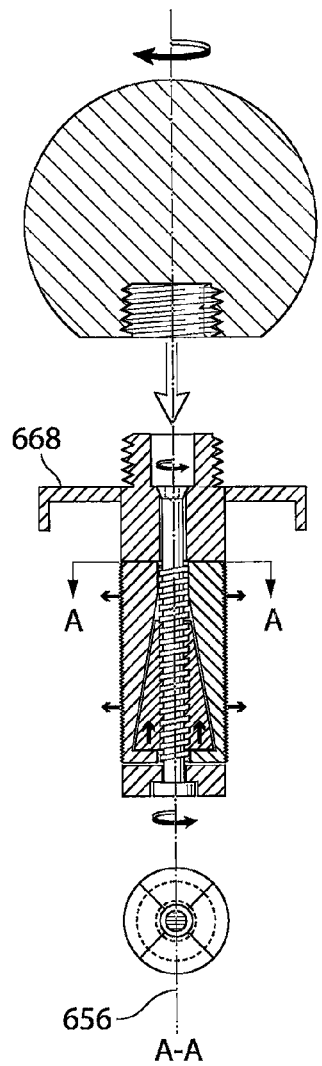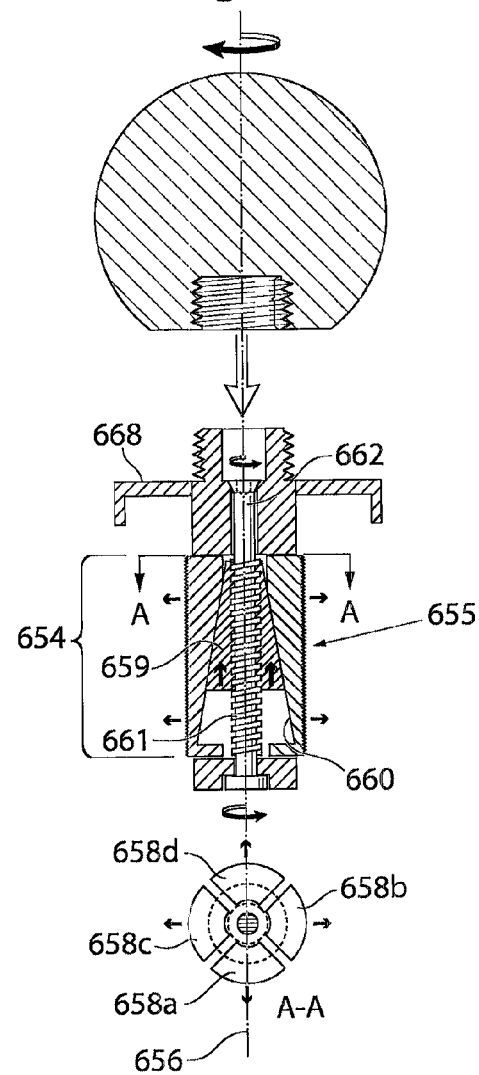

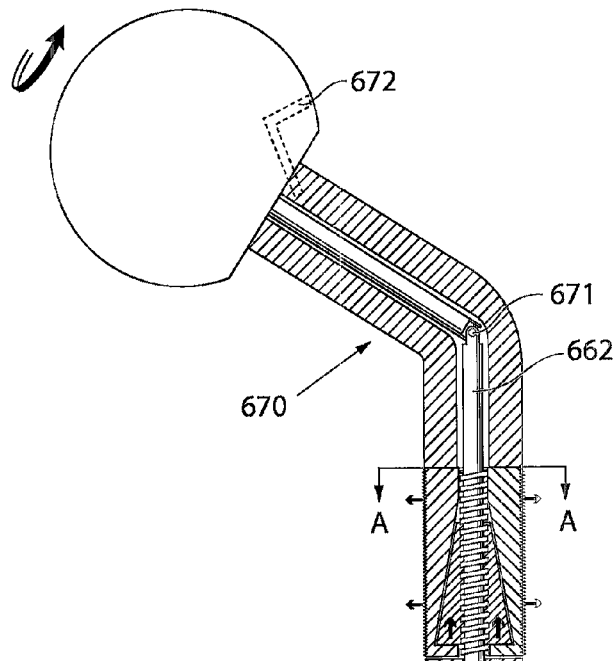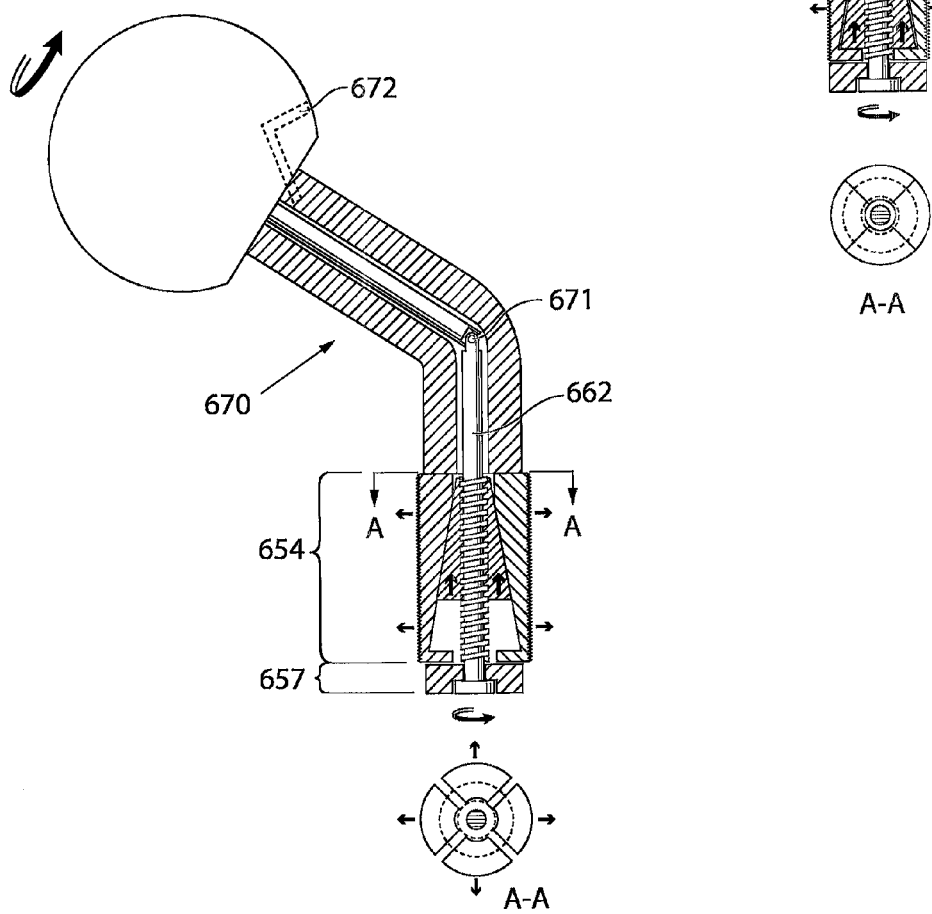

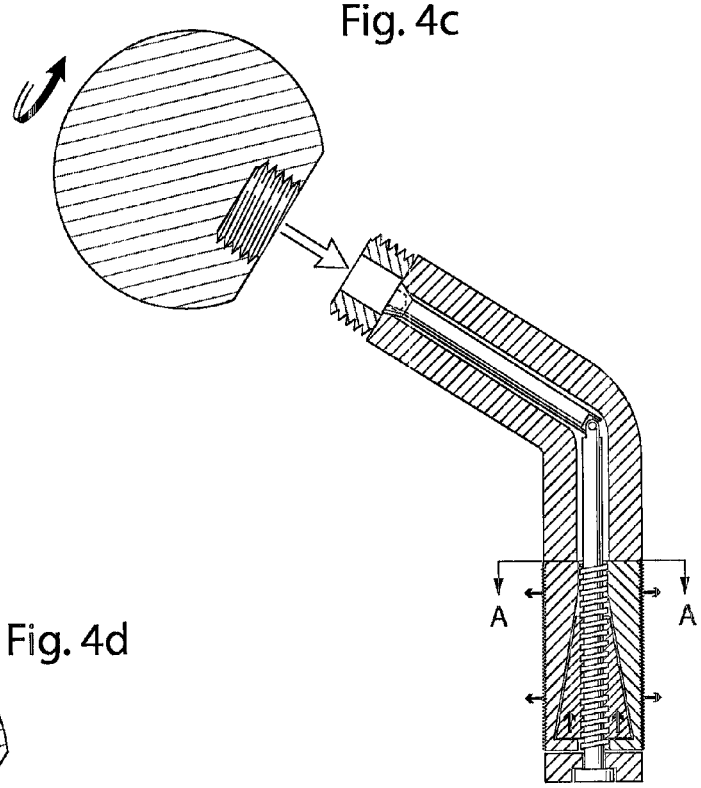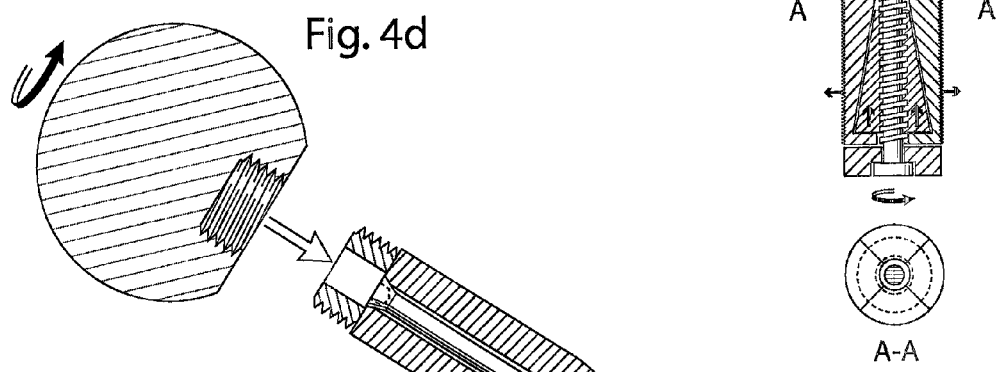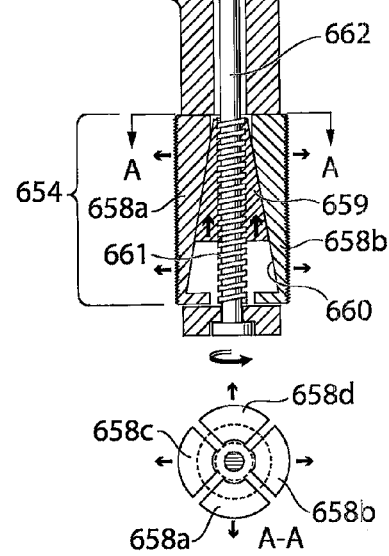

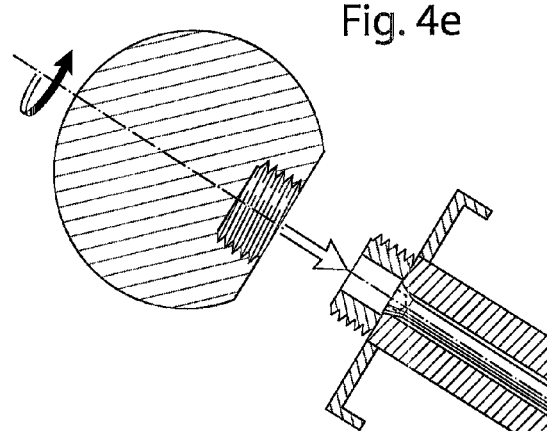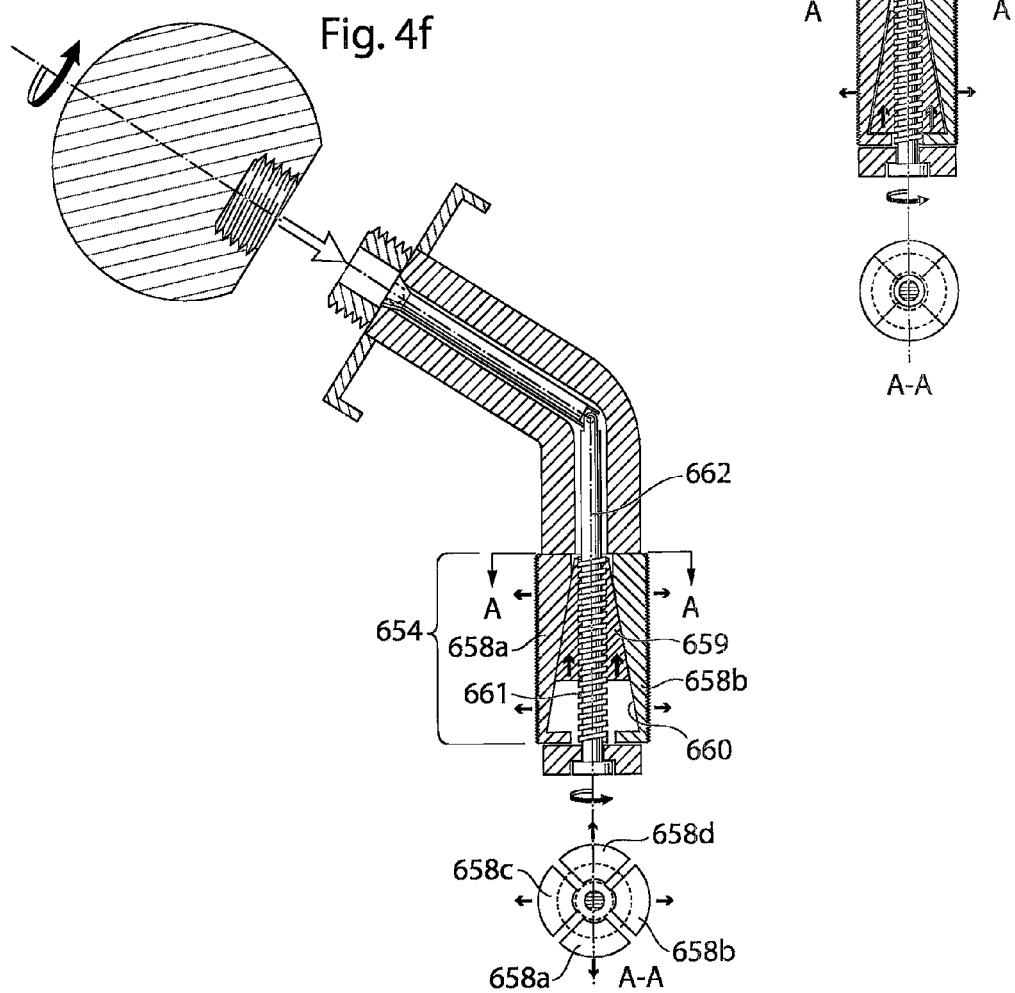
Fig. 4e
Fig. 4f

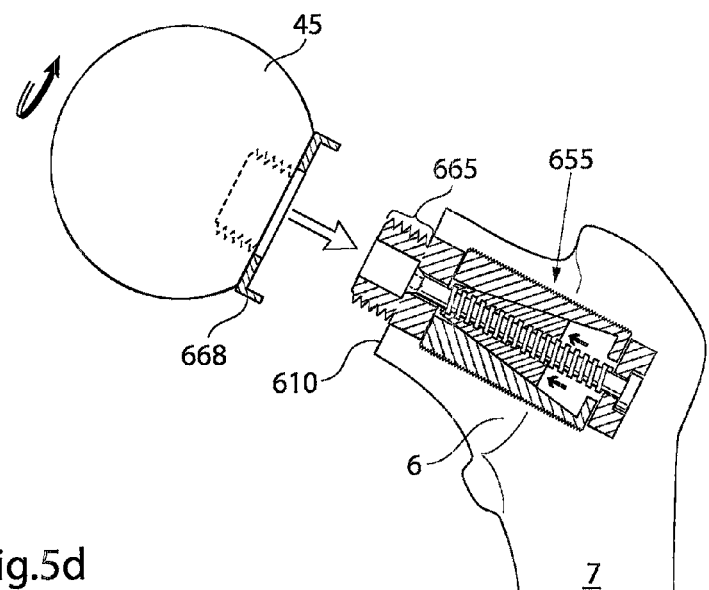
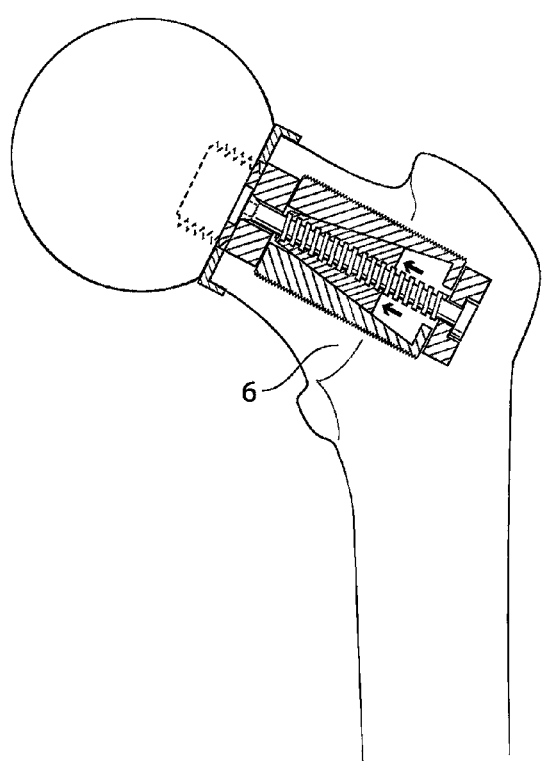

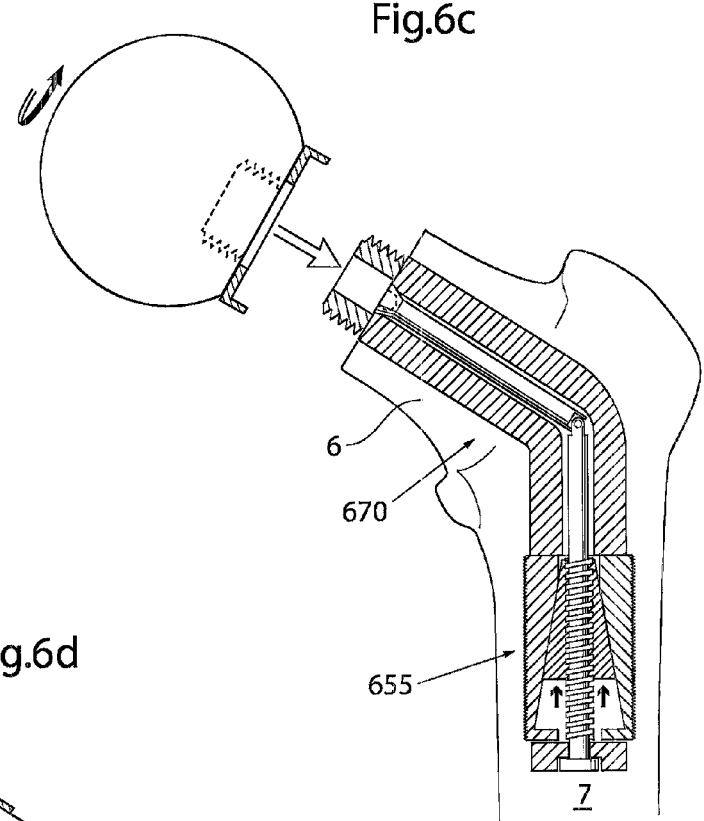
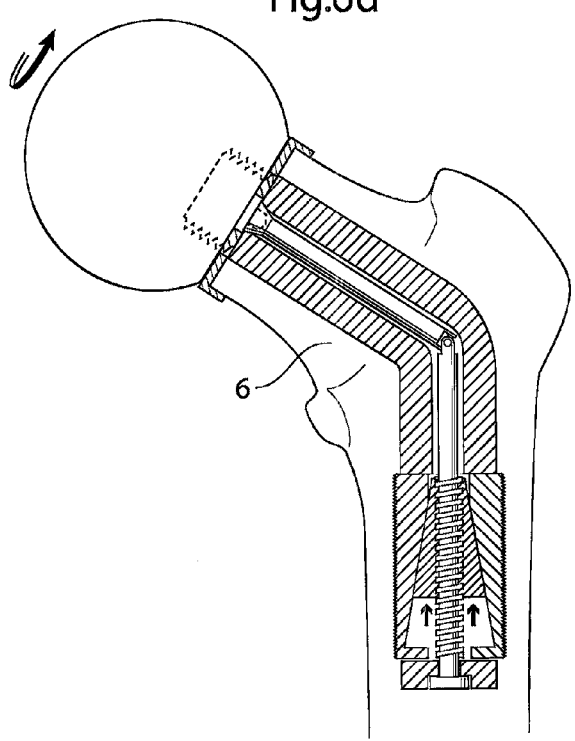

Fig. 7a
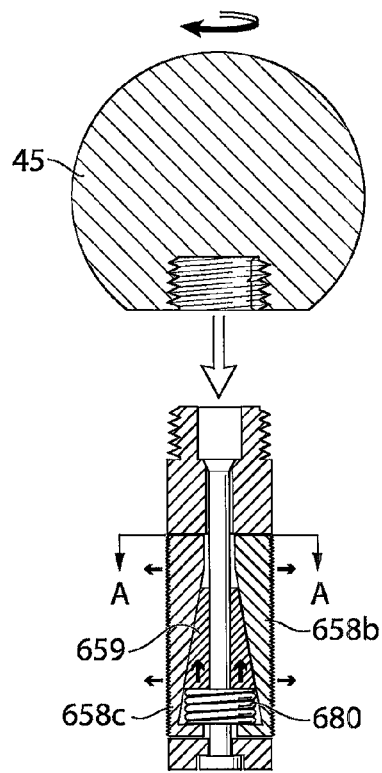
A-A
Fig. 7b
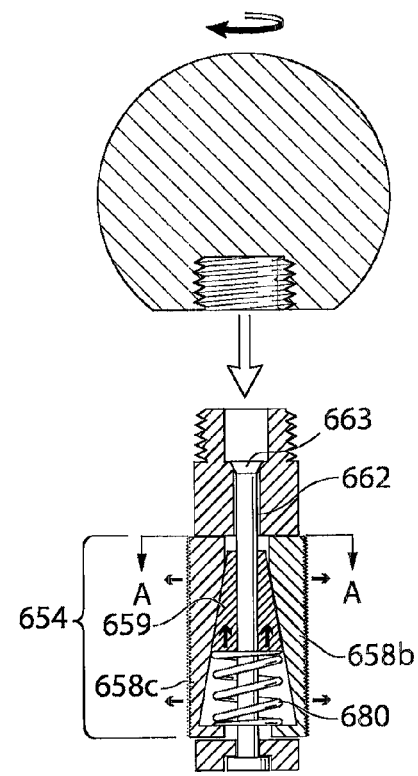
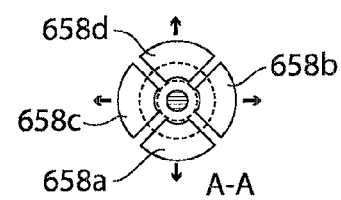

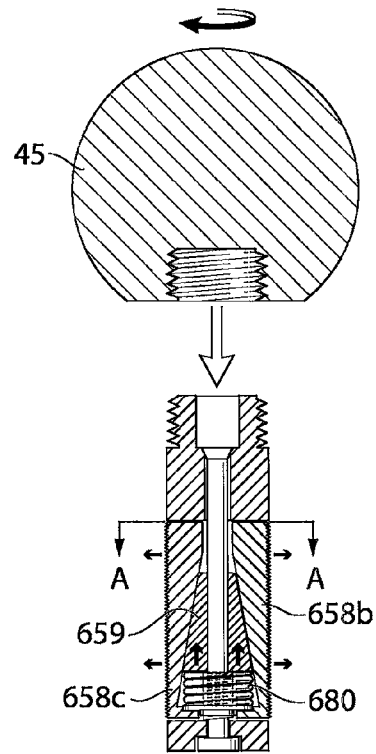
Fig. 8a
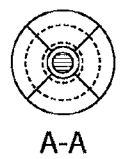
A-A
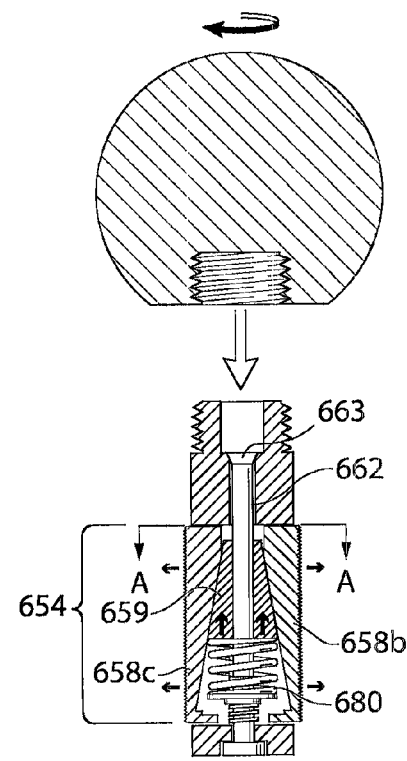
Fig. 8b
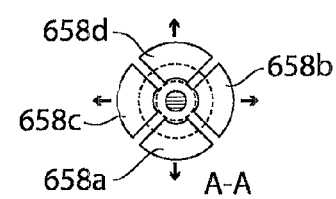
A-A

Fig. 9a
Fig. 9b
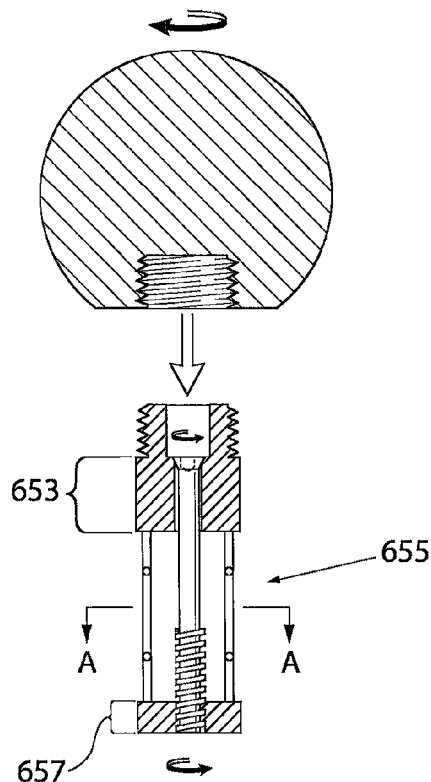
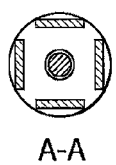
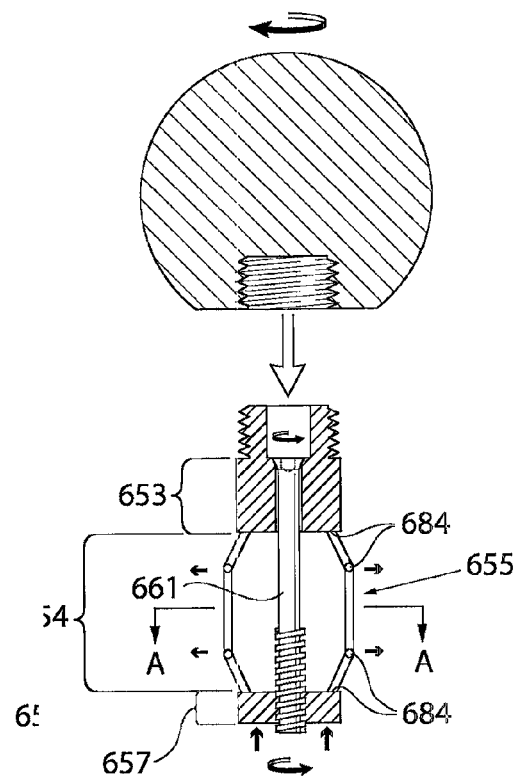
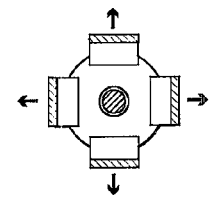

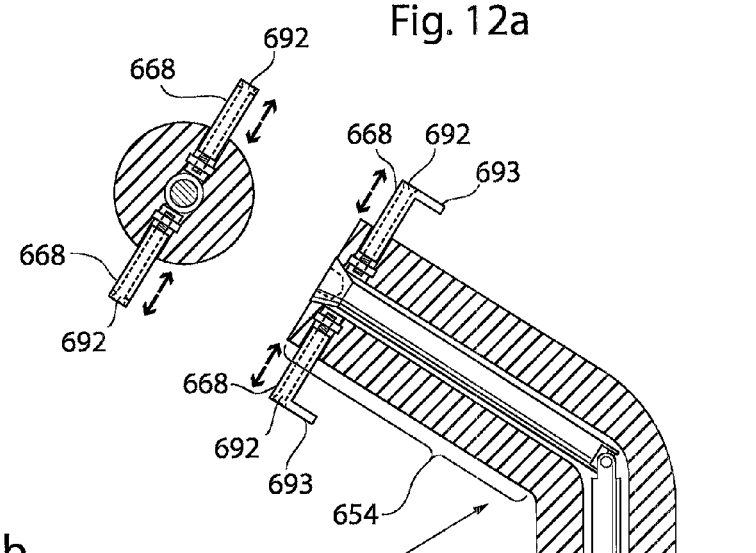
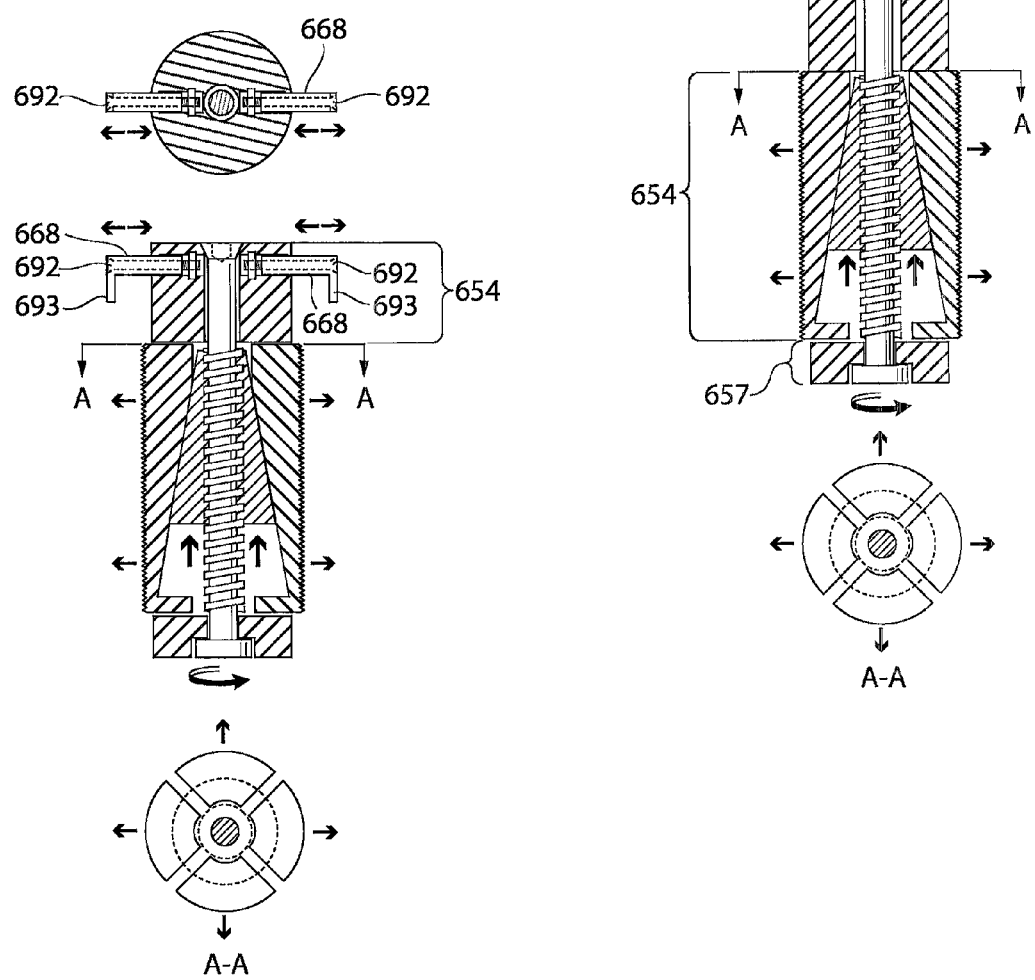
Fig. 12a
Fig. 12b

Fig.16a
Fig.16b
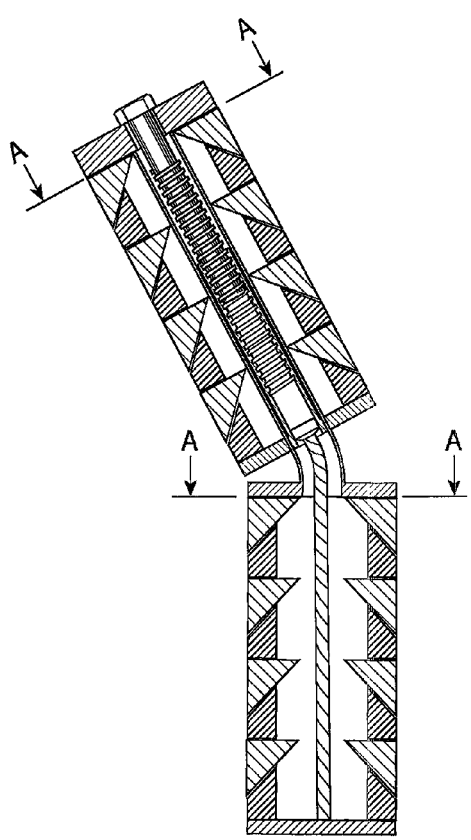
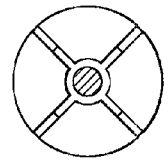
A-A
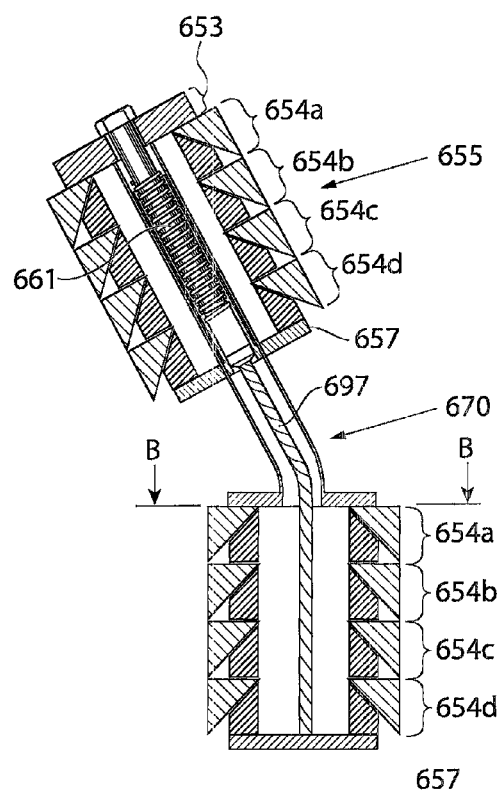
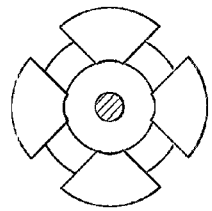
B-B

HIP JOINT DEVICE

This application is the U.S. national phase of International Application No. PCT/SE2010/050804, filed 12 Jul. 2010, which designated the U.S. and claims the benefit of U.S. Provisional Nos.: 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device for implantation in a femoral bone.

BACKGROUND ART

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Iata and the lateral muscles of the thigh. To get access to the joint, the supporting Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A medical device for fixation in a femoral bone of a patient is provided, the medical device comprises: a connecting portion adapted to be connected to a prosthetic hip joint contacting portion, an expanding portion, and a bone contacting surface on the expanding portion. The expanding portion could be adapted to be at least partially inserted into the femoral bone of a patient and to expand within the femoral bone, such that the bone contacting surface is placed in contact with the inside of the femoral bone for fixating the medical device to the femoral bone. By the fixation using an expanding portion a sturdy fixation is achieved without the need to go into or penetrate bone, or the need for fixation using bone cement.

According to one embodiment the medical device comprises a bent portion placed between the connecting portion and an end portion of the medical device, e.g. for adjusting to the anatomy of the femoral bone.

According to one embodiment, the connecting portion could comprise a fixating portion adapted to fixate a prosthetic contacting portion. The fixating portion could comprise a threaded portion, which could enable the screw-fixation of a prosthetic hip joint contacting portion to the connecting portion.

According to one embodiment, the medical device has a centrally placed longitudinal axis reaching from the connecting portion to an end portion, and the expanding portion comprises a plurality of expansion members adapted to expand radially away from the longitudinal axis. By the plurality of expansion members the force from the expansion members is evenly distributed throughout the surface of the inside of the femoral bone.

The medical device could according to any of the embodiments herein have a centrally placed longitudinal axis reaching from the connecting portion to an end portion, and the medical device could comprise a plurality of expanding portions distributed axially along the longitudinal axis of the medical device.

According to one embodiment the medical device could comprise a plurality of expanding portions distributed axially along the longitudinal axis of the medical device and being adapted to radially expand independently of each other to allow different expansion of the different expanding portions.

According to another embodiment the medical device could comprise expanding portions placed between the bent portion and the end portion, or between the bent portion and the connecting portion.

According to yet another embodiment the medical device comprises a first and a second expanding portion, the first expanding portion is placed between the bent portion and the connecting portion, and the second expanding portion is placed between the bent portion and the end portion.

According to yet another embodiment the medical device comprises a plurality of expanding portions distributed axially along a longitudinal axis of the medical device, the plurality of expanding portions are placed between the bent portion and the end portion or between the bent portion and the connecting portion.

According to one embodiment, the expanding portion comprises a deformable expanding portion, wherein the expanding portion expands by the deformable expanding portion deforming, such that the bone contacting surface is placed in contact with the inside of the femoral bone for fixating the medical device to the femoral bone, wherein the deformable expanding portion allows a larger contact with the bone contacting surface.

According to one embodiment, the medical device further comprises an operating device adapted to operate the expanding portion. The operation device could comprising a flexible member in communication with the connecting portion and the end portion, the flexible member adapted to be pulled in the direction of the connecting portion for exerting an axial force on a part of the operating device causing, at least partially, radial expansion of the expanding portion. In other embodiments, the operation device could comprise an elastic operation device adapted to exert an elastic force on the expanding portion. The elastic operation device could for example be a spring.

According to one embodiment, the medical device further comprises an adjustment device for adjusting the tension of the elastic operation device and thus the force exerted by the expansion members. The operating device could further comprise a conical member adapted to contact a corresponding surface of the expanding portion for expanding the expanding portion. In one embodiment, the operating device could comprise a rotatable threaded portion adapted to engage a corresponding threaded portion of the medical device for expanding the expanding portion. The operating device could according to one embodiment comprise a rotatable threaded portion adapted to engage a corresponding threaded portion of the conical member for operating the conical member and thereby the corresponding surface of the expanding portion for expanding the expanding portion.

The bone contacting surface according to any of the embodiments herein could comprise at least one tapered member adapted to at least partially enter the bone of the inside of the collum femur, or the bone contacting surface could comprise a porous micro or nano structure adapted to promote the in-growth of bone in the medical device.

The medical device according to any of the embodiments, could further comprise a stabilizing member, which could be a stabilizing member adapted to be placed in contact with a cut surface of the femoral bone and/or an outer surface of the femoral bone. The stabilizing member could according to one embodiment be operable for exerting a force on the femoral bone for further fixating the medical device to the femoral bone.

The femoral bone comprises a longitudinal axis extending along the femoral bone, and the stabilizing member could according to one embodiment be adapted to extend on the outside of the femoral bone along a stabilizing portion of the longitudinal axis, and the expanding portion could be adapted to extend on the inside of the femoral bone, along at least a portion of the stabilizing portion of the longitudinal axis, such that a portion of the femoral bone is clamped between the expanding portion on the inside of the femoral bone and the stabilizing member on the outside of the femoral bone.

According to one embodiment, the medical device further comprises a prosthetic hip joint contacting portion which could be adapted to be detachably fixated to a fixating portion of the connecting portion. The fixating portion of the prosthetic hip joint contacting portion could comprise a threaded portion corresponding to a threaded portion of the fixating portion of the connecting portion, such that the prosthetic hip joint contacting portion can be screwed on to the connecting portion.

In any of the embodiments herein, the prosthetic contacting portion could comprise a spherical convex contacting portion or a spherical concave contacting portion, and the prosthetic contacting portion could comprises the stabilizing described in relation to any of the embodiments herein.

According to yet another embodiment, the prosthetic contacting portion could be rotatable in relation to the connecting portion, and the prosthetic contacting portion could be mechanically connected to an operating device operating the expanding portion, such that the expanding portion can be expanded by rotating the prosthetic contacting portion. The medical device could further comprise a locking member adapted to lock the prosthetic contacting portion in relation to the connecting portion.

According to one embodiment, the medical device further comprises a locking member adapted to lock the prosthetic contacting portion in relation to the connecting portion.

According to one embodiment, the prosthetic contacting portion comprises an artificial caput femur surface.

A method for mounting anyone of the embodiments herein for fixation of the medical device in a femoral bone of a patient is further provided. The method comprising: cutting the skin, dissecting a hip region of a patient, surgically affecting and open the femoral bone, inserting the expanding portion of the medical device at least partially into the femoral bone, and expanding within the femoral bone the expanding portion such that the bone contacting surface is placed in contact with the inside of the femoral bone for fixating the medical device direct or indirect to the femoral cortical bone.

According to one embodiment, the medical device comprises a plurality of expanding portions distributed axially along a longitudinal axis of the medical device and the method further comprises the steps of; expanding said plurality of expanding portions towards the femoral cortical bone.

According to one embodiment, the medical device further comprises an operating device adapted to operate the expanding portion, and the method further comprises the steps of: operating manually or by a motor the expanding portion to fixate the device towards the femoral cortical bone.

According to one embodiment, the expanding portions is suspended and adjustable to adjust the tension towards the femoral cortical bone, and the method comprises the steps of; adjusting the expanding portion of the device.

Please note that any embodiment or part of embodiment as well as any method or part of method could be combined in any way. All examples herein should be seen as part of the general description and therefore possible to combine in any way in general terms.

BRIEF DESCRIPTION OF DRAWINGS

The invention is now described, by way of example, with reference to the accompanying drawings, in which:

FIG. 1b shows the collum femur in section,

FIG. 3a shows the medical device according to a one embodiment, in a first state, FIG. 3b shows the medical device according to a one embodiment, in a second state, FIG. 3c shows the medical device according to a one embodiment, in a first state, FIG. 3d shows the medical device according to a one embodiment, in a second state, FIG. 3e shows the medical device according to a one embodiment, in a first state, FIG. 3f shows the medical device according to a one embodiment, in a second state, FIG. 4a shows the medical device according to a one embodiment, in a first state, FIG. 4b shows the medical device according to a one embodiment, in a second state, FIG. 4c shows the medical device according to a one embodiment, in a first state, FIG. 4d shows the medical device according to a one embodiment, in a second state, FIG. 4e shows the medical device according to a one embodiment, in a first state, FIG. 4f shows the medical device according to a one embodiment, in a second state, FIG. 5c shows the medical device according to a one embodiment, when placed in a femoral bone, FIG. 5d shows the medical device according to a one embodiment, when placed in a femoral bone, FIG. 6c shows the medical device according to a one embodiment, when placed in a femoral bone, FIG. 6d shows the medical device according to a one embodiment, when placed in a femoral bone, FIG. 7a shows the medical device according to a one embodiment, in a first state, FIG. 7b shows the medical device according to a one embodiment, in a second state, FIG. 8a shows the medical device according to a one embodiment, in a first state, FIG. 8b shows the medical device according to a one embodiment, in a second state, FIG. 9a shows the medical device according to a one embodiment, in a first state, FIG. 9b shows the medical device according to a one embodiment, in a second state, FIG. 12a shows the medical device according to a one embodiment, in a first state, FIG. 12b shows the medical device according to a one embodiment, in a second state, FIG. 16a shows the medical device according to a one embodiment, in a first state, FIG. 16b shows the medical device according to a one embodiment, in a second state,

DETAILED DESCRIPTION

Figure 1:
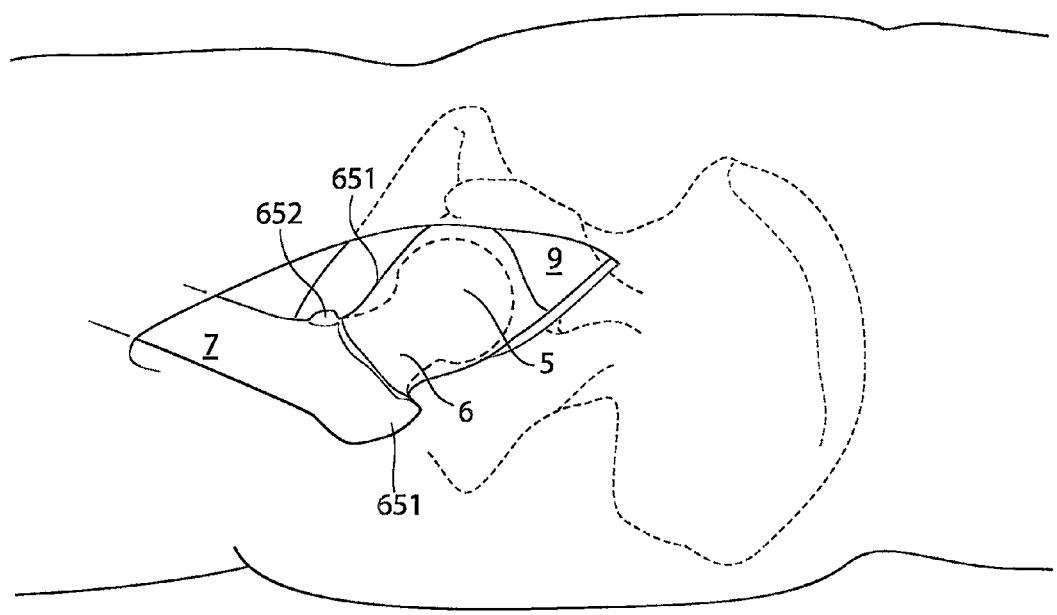
FIG. 1 shows the exposing of the caput femur through an incision in the thigh.

The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

The anatomy of the hip joint and its surroundings is further disclosed in: Marieb et al., Human Anatomy, 2003, Benjamin Cummings, San Francisco, pages 195-202 and in Moore et al., Clinically oriented anatomy, 1999, Lippincott, Williams & Wilkins, Baltimore, pages 501-653, both hereby incorporated by reference.

A severe but yet common complication following hip joint surgery is the loosening of the prosthesis from its fixation in the femoral bone. The loosening could be induced by an abnormal strain being placed on the hip joint from e.g. the patient falling or making a rapid movement of the hip. Most hip joint prosthesis are made from a material harder than the bone to which the prosthesis is fixated, which adds to the tension created between the fixations and the bone of the patient. Bone cement could further be used to fixate prosthesis, which could create a bodily macrophage reaction excavating the bone cement and thus causing loosening of the prosthesis. Other fixations, such as fixations using orthopedic screws penetrating the bone could also create a bodily reaction rejecting the foreign matter of the medical device. Eliminating the use of bone cement and orthopedic screws, and at the same time creating a stabile fixation would be very advantageous, furthermore, creating a fixation that has the ability to move slightly in the fixation in response to exposure to force e.g. from the patient falling would be even more advantageous.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

The functional position of an implantable medical device or prosthesis is the position in which the hip joint can perform functional hip movements.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Elasticity is to be understood as a materials ability to deform in an elastic way.

Stiffness is to be understood as the resistance of an elastic body to deformation by an applied force.

FIG. 1 shows a lateral view of a human patient when a conventional hip joint procedure is being performed. An incision in the thigh region of the patient has been made and the femoral bone 7 comprising the collum femur 6 and the caput femur 5 has been dislocated from its usual position in the hip joint. In the usual position the caput femur 5 is in connection with the acetabulum, which is a part of the pelvic bone 9. The caput femur 5 is fixated to the pelvic bone by means of its articular capsule 650 (capsular ligament), which is a strong and dense capsule that surrounds the collum femur 6, and is attached, to the femoral bone 7, at the intertrochanteric line (the line between the trochanter major 651 and the trochanter minor 652), and to the pelvic bone 9 in the area surrounding the acetabulum. For clarification of further parts of the disclosure, both the caput and collum femur are portions of the femoral bone.

Figure 2A:
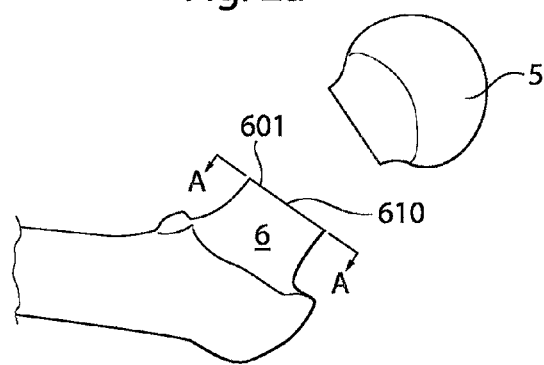
FIG. 2a shows the step of removing a proximal part of the caput femur.

FIG. 2a shows the proximal part of the caput femur 5 being removed e.g. by means of a bone saw. A surface of a section 601 is thus created perpendicularly to a length axis of the collum 6 and caput 5 femur.

Figure 2B:
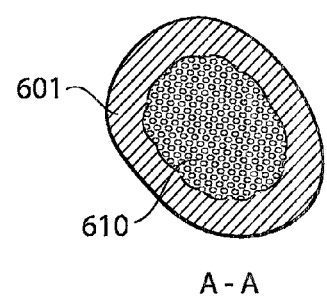
FIG. 2b shows the cross section A-A of the collum femur.

FIG. 2b shows a section A-A of the collum femur 6, as shown in FIG. 2a. The section A-A shows the collum femur 6 (as the rest of the femoral bone) comprising cortical bone 601, the outer more sclerotic bone, and cancellous bone 610, the inner porous bone located in the bone marrow.

FIG. 3a shows a medical device for fixation in the femoral bone of a patient. The medical device comprises a connecting portion 653 connected to a prosthetic contacting portion 45, in the embodiment shown being a convex prosthetic contacting portion 45. The medical device further comprising an expanding portion 654, and a bone contacting surface 655 on the expanding portion 654. The expanding portion 654 is adapted to be at least partially inserted into the femoral bone of a patient and to expand within the femoral bone such that the bone contacting surface 655 is placed in contact with the inside of the femoral bone for fixating the medical device to the femoral bone. The medical device has a centrally placed longitudinal axis 656 reaching from the connecting portion 653 to an end portion 657, and wherein the expanding portion 654 comprises a plurality of expansion members 658a-d, adapted to expand radially away from the longitudinal axis 656.

The medical device further comprises an operating device 659 adapted to operate the expanding portion 564, according to the embodiment shown in FIG. 3a, 3b the operating device 659 comprises a conical member 659 adapted to contact a corresponding surface 660 of the expanding portion 654 for expanding the expanding portion 654. The operating device 659 further comprises a rotatable threaded portion 661 adapted to engage a corresponding threaded portion of the conical member 659 for moving the conical member 659 along the centrally placed longitudinal axis 656 in the direction of the connecting portion 653. The threaded portion 661 is a portion of an elongated member 662, which according to the embodiment shown in FIG. 3a, 3b reaches from the end portion 657 to the top part of the prosthetic contacting portion 45 having a tool engaging portion 663, such that the elongated member 662 can be rotated using a tool for rotating the threaded portion and thereby the moving the conical member 659.

The bone contacting surfaces 655, according to the embodiments shown in FIG. 3a, 3b comprise needle or nail like tapered members 664 adapted to at least partially enter the bone of the inside of the collum femur for further fixating the medical device in the femoral bone, especially axially along the centrally placed longitudinal axis 656. In other embodiments, not shown, the bone contacting surface comprises a porous micro- or nano-structure adapted to promote the in-growth of bone in the medical device. The bone contacting surface 655 is here described in relation to the embodiment of FIGS. 3a and 3b, however the adaptation of the bone contacting surface 655 is equally applicable in all of the embodiments disclosed herein.

FIG. 3b shows the medical device according to the embodiment shown in FIG. 3b when the elongated member 662 has been rotated by means of a tool such that the threaded portion 661 has moved the conical member 659 affecting the corresponding surface of the expansion members 658a-d and thus expanding the expanding portion 654 such that the bone contacting surface 655 is adapted to be placed in contact with the inside of the femoral bone.

FIG. 3c shows the medical device according to an embodiment comprising most elements described with reference to FIGS. 3a and 3b, the difference being that the prosthetic hip joint contacting portion 45 is detachably fixated to a fixating portion 665 of the connecting portion 653. The fixating portion 665 is adapted to engage a fixating portion 667 of the prosthetic hip joint contacting portion 45 for fixating the prosthetic hip joint contacting portion 45 to the connecting portion 653. According to the embodiment shown in FIGS. 3c and 3d the fixating portion 665 and the fixating portion 667 of the prosthetic hip joint contacting portion 45 comprises corresponding threaded portions 666, such that the prosthetic hip joint contacting portion 45 can be screwed on to the connecting portion 653. The elongated member 662, according to the embodiment shown in FIG. 3c, 3d ends at the top of the connecting portion 653, where the tool engaging portion 663 is placed.

FIG. 3d shows the medical device according to the embodiment shown in FIG. 3c when the elongated member 662 has been rotated by means of a tool such that the threaded portion 661 has moved the conical member 659 affecting the corresponding surface 660 of the expansion members 658a-d and thus expanding the expanding portion 654 such that the bone contacting surface 655 is adapted to be placed in contact with the inside of the femoral bone.

FIG. 3e shows the medical device according to an embodiment comprising most elements described with reference to FIGS. 3c and 3d, the difference being that the medical device further comprises a stabilizing member 668 adapted to be placed in contact with a cut surface (610 in FIGS. 2a and 2b) of the femoral bone along the centrally placed longitudinal axis 656 and with the outer surface of the femoral bone, substantially perpendicular to the centrally placed longitudinal axis 656. In the embodiment shown in FIGS. 3e, 3f, the stabilizing member 668 is adapted to be in contact with both the cut surface of the femoral bone and the outer surface of the femoral bone, however, it is equally conceivable that the stabilizing member 668 is used in connection with any of the embodiments herein and adapted to only contact the cut surface of the femoral bone or only contact the outer surface of the femoral bone. The stabilizing member 668 further stabilizes the medical device axially by the contact with the cut surface, and radially by the contact with the outer surface of the femoral bone. The stabilizing member could be adapted to completely encircle the outside of the femoral bone 7 or covering the entire cut surface 610, or the stabilizing member could comprise multiple parts each covering a smaller portion of the cut surface or the outer surface of the femoral bone 7. In the embodiment shown in FIGS. 3e and 3f the medical device is shown in connection with the prosthetic hip joint contacting portion 45 disclosed with reference to FIGS. 3c and 3d, however, it is equally conceivable that the medical device shown in FIGS. 3e and 3f is used in connection with the prosthetic hip joint contacting portions 45 disclosed with reference to FIG. 3a, 3b or 10, 11.

FIG. 3f shows the medical device according to the embodiment shown in FIG. 3e when the elongated member 662 has been rotated by means of a tool such that the threaded portion 661 has moved the conical member 659 affecting the corresponding surface 660 of the expansion members 658a-d and thus expanding the expanding portion 654 such that the bone contacting surface 655 is adapted to be placed in contact with the inside of the femoral bone.

FIG. 4a shows a medical device according to an embodiment in which the expanding portion 654 is identical to the expanding portion of the medical devices disclosed with reference to FIGS. 3a-3f. The medical device according to the embodiment shown in FIGS. 4a and 4b further comprises a bent portion 670 placed between the connecting portion 653 and the end portion 657 of the medical device for placing the expanding portion 654 further down in the femoral bone. The elongated member 662 operating the conical member 659 according to this embodiment comprises a universal joint 671 enabling the bent portion 670 in the elongated member 662 while still maintaining the rotating function of the elongated member 662. In the embodiment disclosed with reference to FIGS. 4a and 4b the elongated member 662 is operated by the elongated member 662 being connected to the prosthetic hip joint contacting portion 45, such that the elongated member 662 is rotated by rotating of the prosthetic hip joint contacting portion 45. The medical device further comprises a locking member 672 adapted to lock the prosthetic contacting portion 45 in relation to the connecting portion 653, such that the prosthesis can be used in a functional hip joint without the prosthetic contacting portion 45 rotating in relation to the connecting portion 653.

In another embodiment (not shown), the medical device comprises two expanding portions, one placed between the end portion 657 and the bent portion 670, and the other one placed between the connecting portion 45 and the bent portion 670.

FIG. 4b shows the medical device according to the embodiment shown in FIG. 4a when the elongated member 662 has been rotated by the prosthetic contacting portion 45 being rotated such that the expanding portion 654 has been expanded.

FIG. 4c shows an embodiment of the medical device similar to the embodiments shown in FIGS. 4a and 4b with the difference that the medical device in the embodiment in FIGS. 4c and 4d has the prosthetic contacting portion described with reference to FIGS. 3c-3f.

FIG. 4d shows the medical device according to the embodiment shown in FIG. 4c when the elongated member 662 has been rotated by means of a tool such that the threaded portion 661 has moved the conical member 659 affecting the corresponding surface 660 of the expansion members 658a-d and thus expanding the expanding portion 654 such that the bone contacting surface 655 is adapted to be placed in contact with the inside of the femoral bone.

FIGS. 4e and 4f shows an embodiment of the medical device similar to the embodiments shown in FIGS. 4c and 4d, the difference being that the medical device further comprises a stabilizing member 668 adapted to be placed in contact with a cut surface (610 in FIGS. 2a and 2b) of the femoral bone along the centrally placed longitudinal axis 656 and with the outer surface of the femoral bone, substantially perpendicular to the centrally placed longitudinal axis 656. In the embodiment shown in FIGS. 3e, 3f, the stabilizing member 668 is adapted to be in contact with both the cut surface of the femoral bone and the outer surface of the femoral bone, however, it is equally conceivable that the stabilizing member 668 is used in connection with any of the embodiments herein and adapted to only contact the cut surface of the femoral bone or only contact the outer surface of the femoral bone. The stabilizing member 668 further stabilizes the medical device axially by the contact with the cut surface, and radially by the contact with the outer surface of the femoral bone. In the embodiment shown in FIGS. 4e and 4f the medical device is shown in connection with the prosthetic hip joint contacting portion 45 disclosed for example with reference to FIGS. 3c and 3d, however, it is equally conceivable that the medical device shown in FIGS. 4e and 4f is used in connection with the prosthetic hip joint contacting portions 45 disclosed for example with reference to FIG. 3a, 3b or 10, 11.

Figure 5A:
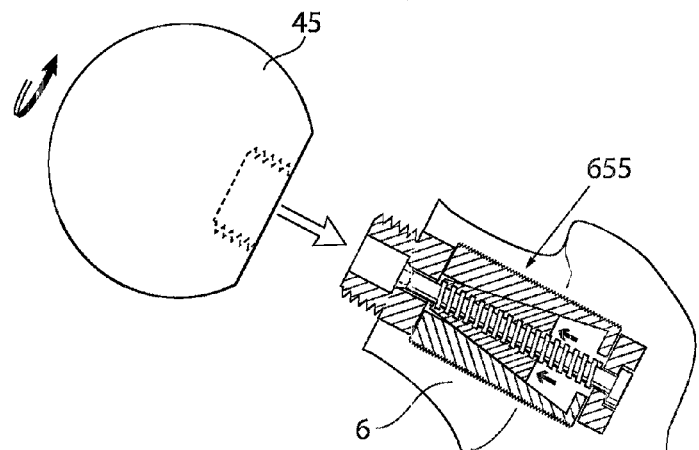
FIG. 5a shows the medical device according to a one embodiment, when placed in a femoral bone.

FIG. 5a shows the medical device described with reference to FIGS. 3c and 3d when placed in the femoral bone 7, particularly in the collum femur 6 portion of the femoral bone 7. The expanding portion has been expanded such that the bone contacting surface (here comprising tapered members) is placed in contact with the inside of the femoral bone.

Figure 5B:
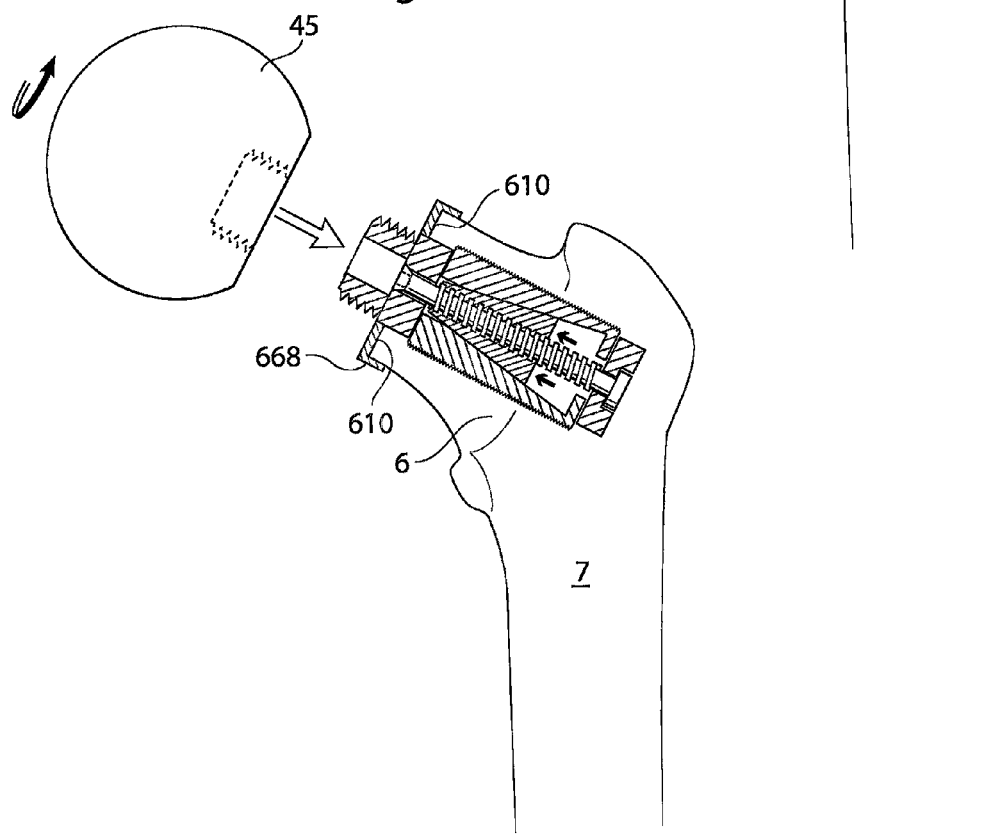
FIG. 5b shows the medical device according to a one embodiment, when placed in a femoral bone.

FIG. 5b shows the medical device described with reference to FIGS. 3e and 3f when placed in the femoral bone 7, particularly in the collum femur 6 portion of the femoral bone 7. The expanding portion has been expanded such that the bone contacting surface (here comprising tapered members) is placed in contact with the inside of the femoral bone. According to this embodiment the medical device further comprises a stabilizing member 668 further stabilizing the medical device axially by the contact with the cut surface 610, and radially by the contact with the outer surface of the femoral bone.

FIG. 5c shows the medical device when placed and expanded in the femoral bone. The medical device shown in FIG. 5c comprises a stabilizing member 668 fixated to the prosthetic hip joint contacting portion 45 such that the stabilizing member is attached to the cut surface 610 and/or the outer surface of the femoral bone when the prosthetic hip joint contacting portion 45 is fixated to the fixating portion 665 (further disclosed with reference to FIG. 3c). The stabilizing member could be adapted to completely encircle the outside of the femoral bone 7 or covering the entire cut surface 610, or the stabilizing member could comprise multiple parts each covering a smaller portion of the cut surface or the outer surface of the femoral bone 7.

FIG. 5d shows the medical device shown in FIG. 5c when fixated to the fixating portion of the medical device, such that the medical device with the prosthetic hip joint contacting surface is in its functional state fixated to the femoral bone 7.

Figure 6A:
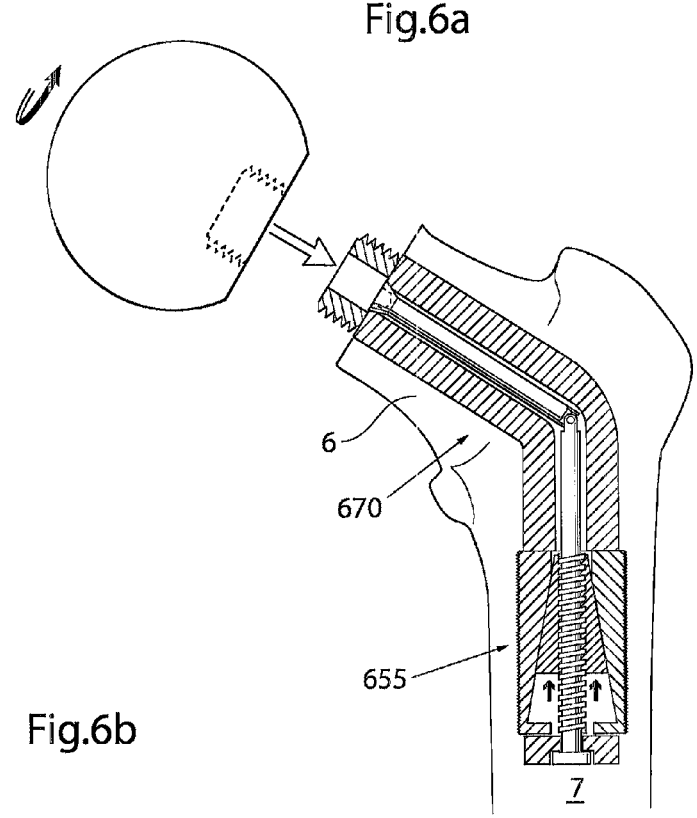
FIG. 6a shows the medical device according to a one embodiment, when placed in a femoral bone.

FIG. 6*a* shows the medical device described with reference to FIGS. 4*c* and 4*d* when placed inside of the femoral bone 7. The expanding portion has been expanded such that the bone contacting surface 655 is placed in contact with the inside of the femoral bone. The bent portion 670 is anatomically adapted to fit in the natural bend of the femoral bone in the area of the intertrochanteric line.

Figure 6B:
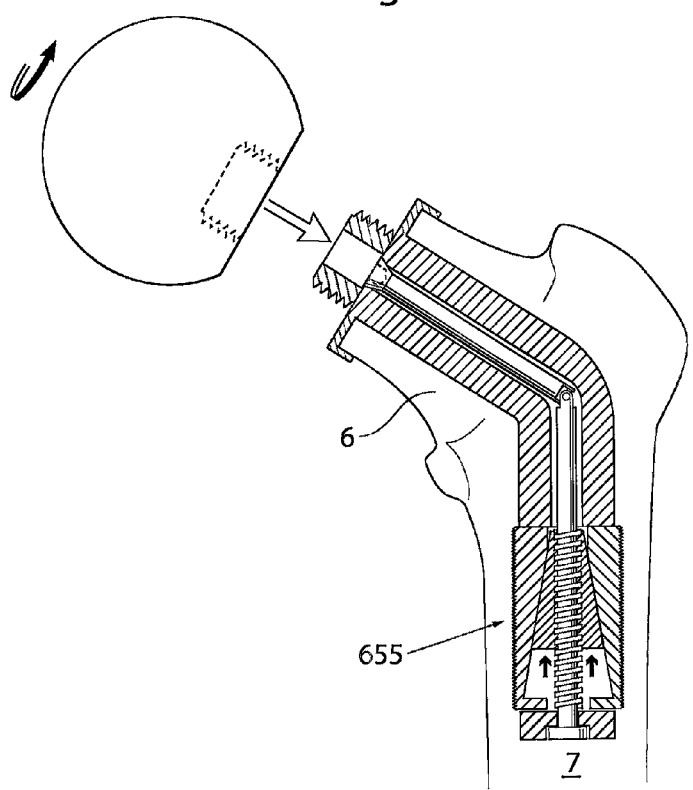
FIG. 6b shows the medical device according to a one embodiment, when placed in a femoral bone.

FIG. 6*b* shows the medical device described with reference to FIGS. 4*e* and 4*f* when placed inside of the femoral bone 7. The expanding portion has been expanded such that the bone contacting surface 655 is placed in contact with the inside of the femoral bone, and the stabilizing portion is placed in contact with the cut surface of the femoral bone 7 and outside of the femoral bone 7. The bent portion 670 is anatomically adapted to fit in the natural bend of the femoral bone in the area of the intertrochanteric line.

FIG. 6*c* shows the medical device described with reference to FIGS. 4*c* and 4*d*, with a stabilizing member 668 fixated to the prosthetic hip joint contacting portion 45, as in the embodiment shown with reference to FIG. 5*c*, such that the stabilizing member is attached to the cut surface 610 and/or the outer surface of the femoral bone when the prosthetic hip joint contacting portion 45 is fixated to the fixating portion 665 (further disclosed with reference to FIG. 3*c*). The stabilizing member could be adapted to completely encircle the outside of the femoral bone 7 or covering the entire cut surface 610, or the stabilizing member could comprise multiple parts each covering a smaller portion of the cut surface or the outer surface of the femoral bone 7. The medical device is here shown when placed inside of the femoral bone 7. The expanding portion has been expanded such that the bone contacting surface 655 is placed in contact with the inside of the femoral bone. The bent portion 670 is anatomically adapted to fit in the natural bend of the femoral bone 7 in the area of the intertrochanteric line.

FIG. 6*d* shows the medical device shown in FIG. 6*c* when fixated to the fixating portion of the medical device, such that the medical device with the prosthetic hip joint contacting surface is in its functional state fixated to the femoral bone 7.

FIGS. 7*a* and 7*b* shows the medical device in an embodiment similar to the embodiment disclosed with reference to FIGS. 3*c* and 3*d*, however in the embodiment of FIGS. 7*a* and 7*b* the operation device of the medical device further comprises an elastic operation device 680 adapted to press on the conical member 659 for expanding the expanding portion 654. The elastic member could be adapted to be released after the insertion of the medical device into the femoral bone 5 thereby creating an elastic pressure on the expansion members 658*a*, 658*b* for elastically pressing the bone contacting surfaces 655 onto the inside of the femoral bone. The elastic operation device 680 is according to the embodiment shown in FIGS. 7*a* and 7*b* released by turning the elongated member 662 with a tool engaging the tool engaging portion 663. The elastic portion enables a fixation of the medical device to the femoral bone that has the ability to move slightly in the fixation in response to exposure to force e.g. from the patient falling. In the embodiment shown in FIGS. 7*a* and 7*b* the elastic operation device is a spring which could be a linear spring or a non-linear spring allowing a first movement with a first elasticity and further movement with a second elasticity that requires greater force. The elastic operation device could according to other embodiments comprise an elastic material, such as an elastomer.

FIG. 7*b* shows the medical device when the elastic operation device 680 has been released such that the expanding portion has been expanded pressing the bone contacting surfaces against the inside of the femoral bone 7.

FIGS. 8*a* and 8*b* shows an embodiment of the medical device comprising the elements described with references to FIGS. 7*a* and 7*b*, with the addition of an adjustment device 681 for adjusting the tension of the elastic operation device 680 and thus the force exerted by the expansion members 658*a-d*. The adjustment device 681 is adjusted by means of the elongated member 662 comprising a threaded portion 682 which interacts with a corresponding threaded portion of the adjustment device 681.

FIG. 8*b* shows the medical device when the elastic operation device 680 has been released such that the expanding portion has been expanded pressing the bone contacting surfaces against the inside of the femoral bone 7, the adjustment device can now be used to adjust the tension of the elastic operation device 680.

FIGS. 9*a* and 9*b* shows the medical device according to an embodiment in which the expanding portion 654 comprises a deformable expanding portion 654, wherein the expanding portion expands by the deformable expanding portion 654 deforming, such that the bone contacting surface 655 is placed in contact with the inside of the femoral bone for fixating the medical device to the femoral bone. The deformable expanding portion 654 deforms at deformation points 684 by the threaded member 661 pulling the end portion 657 towards the connecting portion 653 thus expanding the expanding portion 654 pushing the bone contacting surfaces 655 radially such that they are placed in contact with the inside of the bone of the femoral bone.

FIG. 9*b* shows the medical device when the deformable expanding portion 654 has expanded pressing the bone contacting surfaces 655 against the inside of the femoral bone 7.

Figure 10:
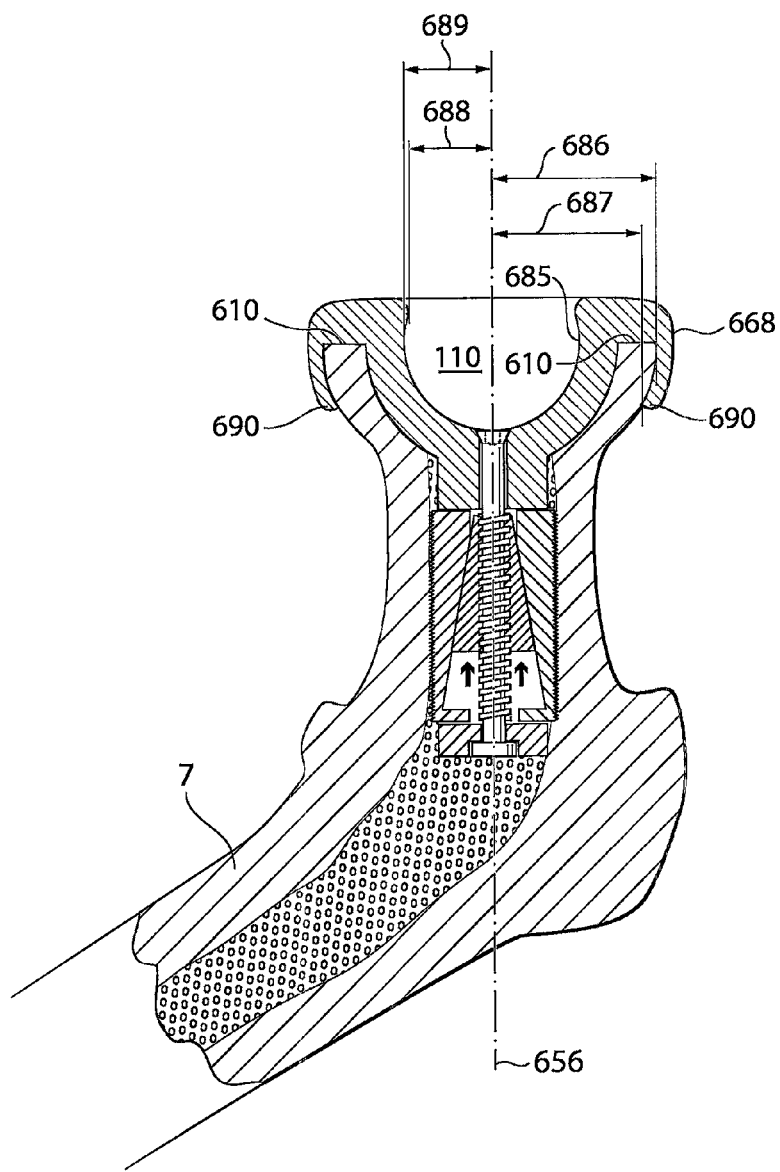
FIG. 10 shows the medical device according to a one embodiment, when placed in a femoral bone.

FIG. 10 shows the medical device according to an embodiment in which the prosthetic contacting portion comprises a spherical concave contacting portion 110 in which a spherical convex contacting portion fixated to the pelvic bone is adapted to be placed. The prosthetic spherical concave contacting portion 110 has a centrally placed longitudinal axis 656 along which the prosthetic spherical concave contacting portion 110 is placed. The prosthetic spherical concave contacting portion 110 has a largest radius 689 perpendicular to the centrally placed longitudinal axis 656 and a clasping portion 685 having a radius 688 perpendicular to the centrally placed longitudinal axis 656 being shorter than the largest radius 689, such that the prosthetic spherical concave contacting portion 110 can clasp a spherical convex contacting portion for fixation of the spherical convex contacting portion in the spherical concave contacting portion. The stabilizing member 668 is according to this embodiment integrated in the spherical concave contacting portion 110 and is placed in connection with the cut surface of the femoral bone, here at the area of the caput femur, and the outer surface of the femoral bone 7. The stabilizing member 668 has a largest inner radius 686 to the centrally placed longitudinal axis 656 and a clasping portion 690 having a shorter radius 687 to the centrally placed longitudinal axis 656, such that the stabilizing member clasps a portion of the caput femur for mechanically fixating the spherical concave contacting portion 110 to the femoral bone 7.

Figure 11A:
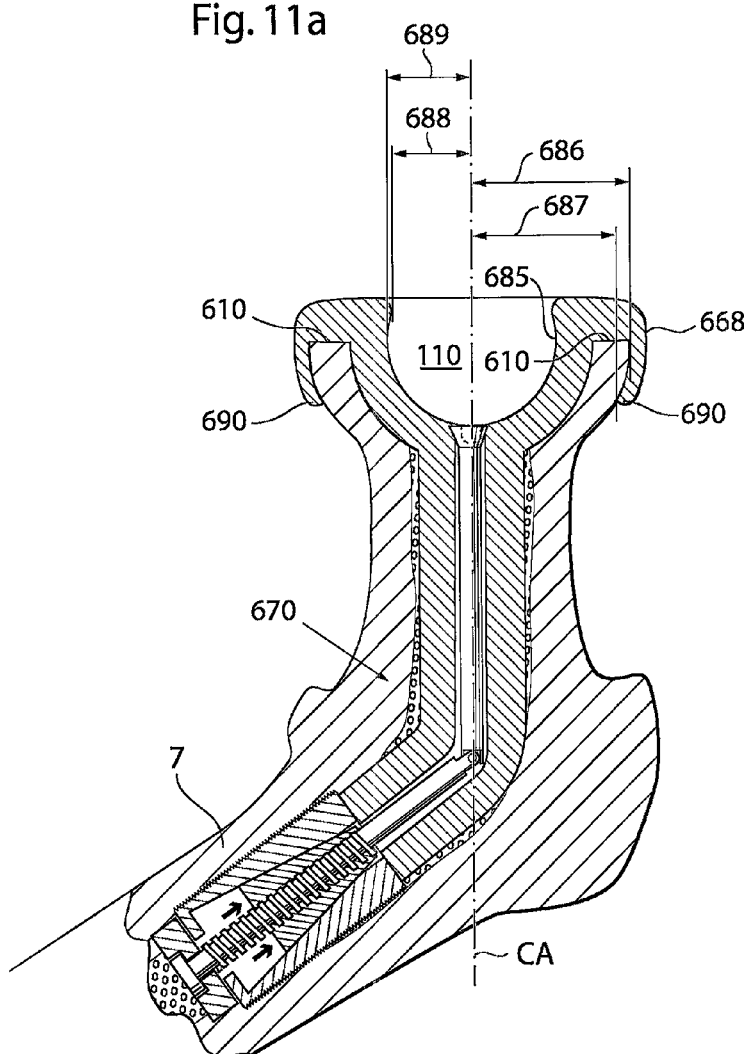
FIG. 11a shows the medical device according to a one embodiment, when placed in a femoral bone.

FIG. 11a shows the medical device according to an embodiment in which the spherical concave contacting portion 110 is identical to the spherical concave contacting portion 110 described with reference to FIG. 10. The difference in the embodiment described with reference to FIG. 11a is that the medical device comprises a bend 670 and that the expanding portion is placed between the bend 670 and the end portion 657. In other embodiments, the clasping portions 690 could be operable or adjustable for further fixating the medical device to the cortical bone, such as disclosed with reference to FIGS. 12a, 12b. The clasping portions 690 could be operable for example by means of a screw for tightening the clasping portions 690 to the cortical bone, which could squeeze the cortical bone between the clasping portions 690 and the part of the medical device placed inside of the femoral bone.

Figure 11B:
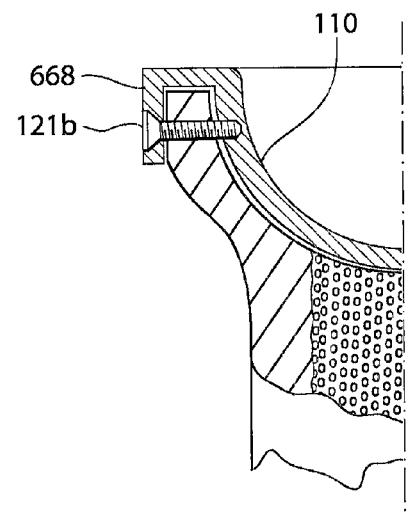
FIG. 11b shows a portion of the medical device and the femoral bone, in section.

FIG. 11b shows an embodiment similar to toe embodiment disclosed with reference to FIG. 11a with the difference that an orthopedic screw 121b is placed between the stabilizing member 668 and the spherical concave contacting portion 110, penetrating the cortical bone of the femoral bone. The orthopedic screw 121b could in other embodiments be used in combination with the clasping portion 690 disclosed with reference to FIG. 11a for further fixating the medical device to the femoral bone.

The spherical concave contacting portion as shown in FIGS. 10 and 11 is shown as fixedly fixated to the connecting portion, however, it is equally conceivable that the spherical concave contacting portion is fixated to the connecting section in accordance with the principles described with reference to FIGS. 3c and 3d or 4a and 4b.

FIGS. 12a and 12b shows the medical device according to an embodiment in which the medical device comprises an operable stabilizing member 668, operable for exerting a force on the femoral bone for further fixating the medical device to the femoral bone. The operable stabilizing member 668 comprises a clamping portion 693 operable by means of an operation screw 692 for clamping a portion of the femoral bone between the clamping portion 693 and the connecting portion 654 of the medical device. The difference between the embodiments of FIGS. 12a and 12b is that the embodiment of FIG. 12a comprises a bent portion 670 such that the expanding portion 654 is placed between the bent portion 670 and the end portion 657.

Figure 13:
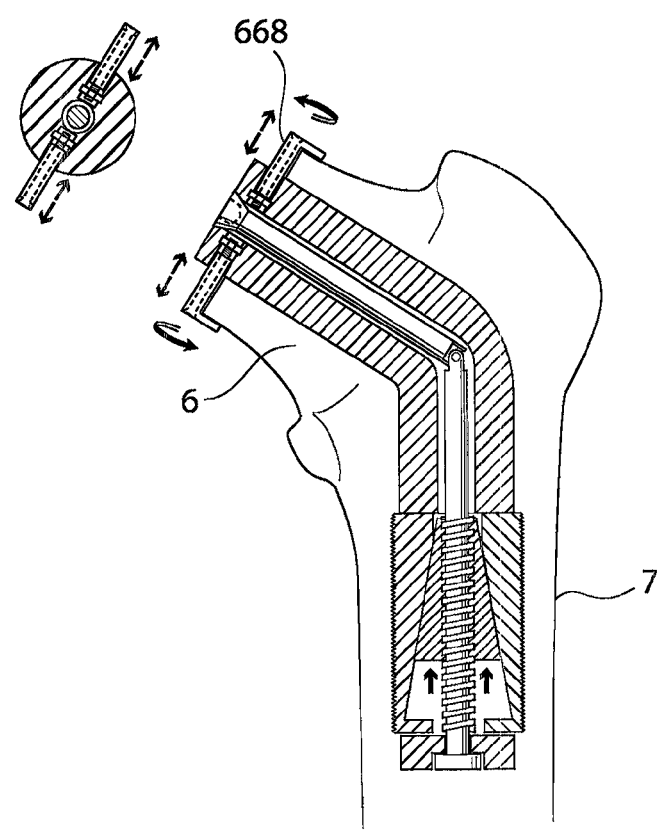
FIG. 13 shows the medical device according to a one embodiment, when placed in a femoral bone.

FIG. 13 shows the medical device according to the embodiment shown in FIG. 12a when positioned inside of the femoral bone 7. The operable stabilizing member 668 has been operated for clamping a portion of the femoral bone 7 for further fixating the medical device to the femoral bone.

Figure 14:
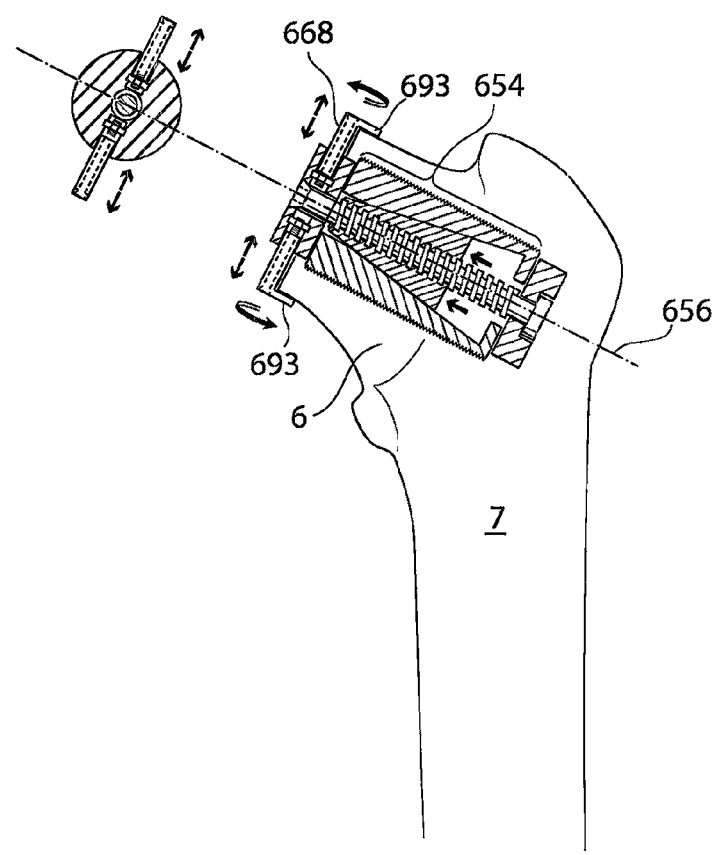
FIG. 14 shows the medical device according to a one embodiment, when placed in a femoral bone.

FIG. 14 shows the medical device according to an embodiment in which the medical device comprises a longitudinal axis 656 extending along the femoral bone 7. The stabilizing member extends on the outside of the femoral bone 7 along a stabilizing/clamping portion, and wherein the expanding portion 654 is extending on the inside of the femoral bone 7, along at least a portion of the stabilizing portion 693 of the longitudinal axis 656, such that a portion of the femoral bone 7 is clamped between the expanding portion 654 on the inside of the femoral bone 7 and the stabilizing member 686 on the outside of the femoral bone 7.

Figure 15A:
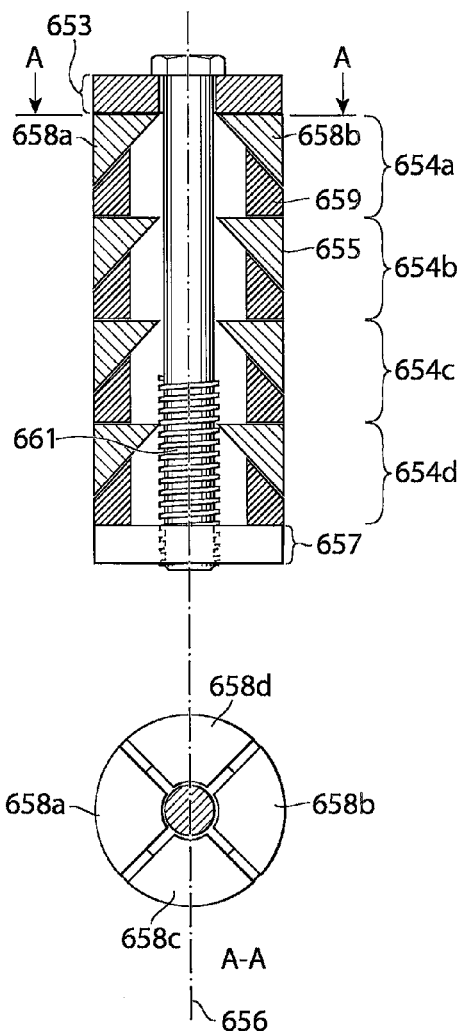
FIG. 15a shows the medical device according to a one embodiment, in a first state.

FIG. 15a shows the medical device according to an embodiment in which the medical device has a centrally placed longitudinal axis 656 reaching from the connecting portion 653 to an end portion 657, wherein the medical device comprises a plurality of expanding portions 654a-d, distributed axially along the longitudinal axis 656 of the medical device. The plurality of expanding portions 654a-d distributed axially along the longitudinal axis 656 of the medical device is adapted to radially expand independently of each other, to allow different expansion of the different expanding portions 654a-d. The different expansion could allow the expanding portions 654a-d to adapt to the uneven surfaces of the anatomy of the inside of the femoral bone. Since the different expanding portions expand independently of each other, one expanding portion 654a will expand until the bone contacting surface 655 of that particular expanding portion is placed in contact with the bone of the inside of the femoral bone, after which the other expanding portions 654b-d will continue to expand until their respective bone contacting surface is placed in contact with the inside of the femoral bone. Each expanding portion comprises four expansion members 658a-d each having a sloped surface 660 corresponding to a sloped surface 696 of the conical members 659, such that the conical members presses the expansion members radially from the longitudinal axis 656 when the conical members 659 are moved in the direction of the connecting portion 653.

Figure 15B:
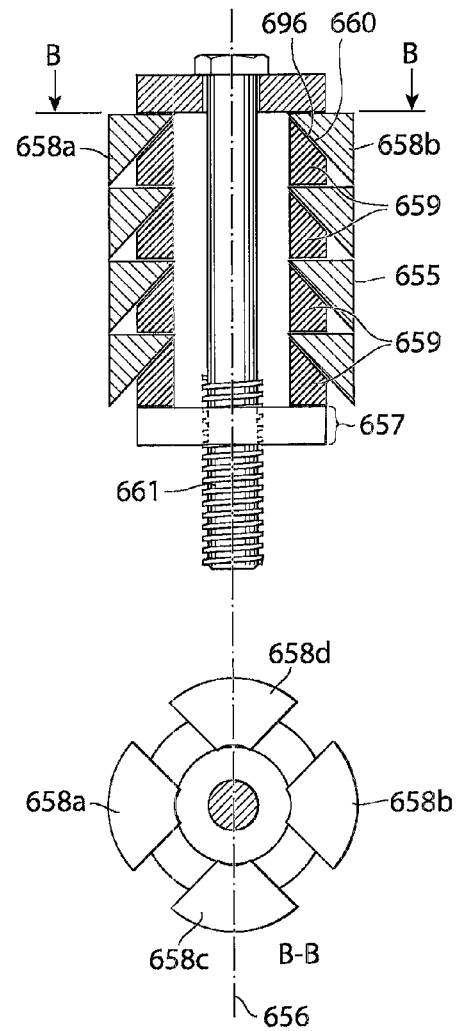
FIG. 15b shows the medical device according to a one embodiment, in a second state.

FIG. 15b shows the medical device when the expanding portions 654a-d has been expanded for pressing the bone contacting surfaces 655 against the inside of the femoral bone 7.

FIG. 16a shows an embodiment of the medical device similar to the embodiment disclosed with reference to FIGS. 15a and 15b, the difference being that the embodiment of FIGS. 16a and 16b comprises a bent portion 670 and that a plurality of expanding portions are placed both between the bent portion 670 and the connecting portion 653, and between the end portion 657 and the bent portion 670 such that the medical device can be fixated by expanding portions 654 expanding both in the collum area of the femoral bone and in an area below the intertrochanteric line. However, it is equally conceivable in other embodiments that the plurality of expanding portions 654 are place only between the bent portion 670 and the connecting portion 653 or only between the end portion and the bent portion 670. The threaded portion is fixated to a flexible member 697 such that the flexible member 697 is in communication with the connecting portion 653 and the end portion 657, the flexible member 697 being adapted to be pulled in the direction of the connecting portion 653 for exerting an axial force on a expanding portions 654a-d causing radial expansion of the expanding portions. The flexible member 697 could for example be a wire.

16b shows the medical device when the expanding portions 654a-d has been expanded for pressing the bone contacting surfaces 655 against the inside of the femoral bone 7.

The embodiments disclosed with reference to FIGS. 15 and 16 could be used in combination with any prosthetic hip joint contacting portion, such as the contacting portions disclosed with reference to FIGS. 3a, 3c, 4a and 10.

The stabilizing member disclosed throughout the description and/or the medical device comprising the expanding portion disclosed throughout the description, could be further fixated using an adhesive, such as bone cement, or a mechanical fixation element, such as orthopedic screws.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that contacting portions, the elastic operation device, or the entire medical device comprises a metal alloy, such as cobalt-chromium-molybdenum or titanium or stainless steel. Further conceivable materials are polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone, such as the bone contacting surface, could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting portions could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting portions or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian™ or acrylic polymers.

Please note that any embodiment or part of embodiment as well as any method or part of method could be combined in any way. All examples herein should be seen as part of the general description and therefore possible to combine in any way in general terms.

The invention claimed is:

1. A medical device for fixation in a femoral bone of a patient, the medical device comprising:
   a. a connecting portion adapted to be connected to or integrated in a prosthetic contacting portion, and
   b. a plurality of expanding portions, each of which having a bone contacting surface, wherein the expanding portions are adapted to be at least partially inserted into the femoral bone of a patient and to expand within the femoral bone such that the bone contacting surface is placed in contact with the inside of the femoral bone for fixating the medical device directly or indirectly to the femoral cortical bone, wherein the medical device further comprises an operation device comprising:
   a conical member adapted to press on the plurality of expanding portions for operating the plurality of expanding portions, and
   an elastic operation device connected to the conical member and adapted to continuously exert an elastic force on the conical member, such that the elastic force is transferred to the bone contacting surface of the expanding portions, when the medical device is implanted.

2. The medical device according to claim 1, wherein the medical device comprises a bent portion placed between the connecting portion and an end portion of the medical device.

3. The medical device according to claim 2, wherein the medical device comprises a first and a second expanding portion, and wherein the first expanding portion is placed between the bent portion and the connecting portion, and the second expanding portion is placed between the bent portion and the end portion.

4. The medical device according to claim 2, wherein the plurality of expanding portions are placed between the bent portion and the end portion.

5. The medical device according to claim 2, wherein the plurality of expanding portions are placed between the bent portion and the connecting portion.

6. The medical device according to claim 1, wherein the connecting portion comprises a fixating portion adapted to fixate a prosthetic contacting portion.

7. The medical device according to claim 6, wherein the fixating portion comprises a threaded portion.

8. The medical device according to claim wherein the medical device has a centrally placed longitudinal axis reaching from the connecting portion to an end portion, and wherein the plurality of expanding portions comprise a plurality of expansion members adapted to expand radially away from the longitudinal axis.

9. The medical device according to claim 1, wherein the elastic operation device is a spring.

10. The medical device according to claim 1, wherein the medical device further comprises an adjustment device for adjusting the tension of the elastic operation device and this the force exerted by the expanding portions.

11. The medical device according to claim 1, further comprising a rotatable threaded portion adapted to engage a corresponding threaded portion of an adjustment device for adjusting a tension of the elastic operation device.

12. The medical device according to claim 1, wherein the medical device further comprises a stabilizing member adapted to at least one of;
   be placed in contact with a cut surface of the femoral cortical bone,
   be placed in contact with an outer surface of the femoral bone,
   be placed in contact with a cut surface of the femoral cortical bone and an outer surface of the femoral bone, and
   be operable for exerting a force on the femoral bone for further fixating the medical device to the femoral hone.

13. The medical device according to claim 12, wherein the femoral bone comprises a longitudinal axis extending along the femoral bone, and wherein the stabilizing member is adapted to extend on the outside of the femoral bone along a stabilizing portion parallel to the longitudinal axis, and wherein the expanding portions are adapted to extend on the inside of the femoral bone, along at least a portion of the stabilizing portion, such that a portion of the femoral bone is clamped between the expanding portion on the inside of the femoral bone and the stabilizing member on the outside of the femoral bone, for stabilizing the medical device at the femoral cortical bone, directly or indirectly.

14. The medical device according claim 1, wherein the medical device further comprises a locking member adapted to lock the prosthetic contacting portion in relation to the connecting portion.

15. The medical device according to claim 1, wherein at least one bone contacting surface on the plurality of expanding portions comprises a porous micro or nano structure adapted to promote the ingrowth of bone in the medical device.

* * * * *